US008678003B2

(12) United States Patent  
Darkin et al.

(10) Patent No.: US 8,678,003 B2  
(45) Date of Patent: Mar. 25, 2014

(54) VENT SYSTEM FOR CPAP PATIENT INTERFACE USED IN TREATMENT OF SLEEP DISORDERED BREATHING

(75) Inventors: Donald Darkin, Dural (AU); Patrick John Mcauliffe, Chatswood (AU)

(73) Assignee: Resmed Limited, Bella Vista (AU)

( * ) Notice: Subject to any disclaimer, the term of this patent is extended or adjusted under 35 U.S.C. 154(b) by 1887 days.

(21) Appl. No.: 10/579,221

(22) PCT Filed: Nov. 25, 2004

(86) PCT No.: PCT/AU2004/001650  
§ 371 (c)(1),  
(2), (4) Date: Aug. 22, 2006

(87) PCT Pub. No.: WO2005/051468  
PCT Pub. Date: Jun. 9, 2005

(65) Prior Publication Data  
US 2007/0095350 A1     May 3, 2007

Related U.S. Application Data

(60) Provisional application No. 60/524,728, filed on Nov. 25, 2003, provisional application No. 60/538,507, filed on Jan. 26, 2004, provisional application No. 60/550,319, filed on Mar. 8, 2004.

(51) Int. Cl.  
*A62B 9/02* (2006.01)  
*A62B 18/00* (2006.01)

(52) U.S. Cl.  
USPC ............ 128/207.12; 128/205.23; 128/205.24; 128/205.25; 128/206.21; 128/207.13

(58) Field of Classification Search  
USPC ............ 128/205.23, 205.24, 205.25, 206.12, 128/206.16, 206.21, 207.12, 207.13, 128/207.16, 207.18  
See application file for complete search history.

(56) References Cited

U.S. PATENT DOCUMENTS

| | | | | |
|---|---|---|---|---|
| 1,125,542 A | * | 1/1915 | Humphries | 128/207.18 |
| 2,378,468 A | | 6/1945 | Deming | |
| 3,097,642 A | * | 7/1963 | Russell | 128/205.17 |
| 3,152,588 A | * | 10/1964 | Rogowski | 128/206.12 |
| 3,850,171 A | * | 11/1974 | Ball et al. | 128/204.25 |
| 3,913,607 A | | 10/1975 | Price | |
| 3,977,432 A | * | 8/1976 | Vidal | 137/889 |

(Continued)

FOREIGN PATENT DOCUMENTS

| | | |
|---|---|---|
| GB | 1 548 374 | 7/1979 |
| JP | 2-136644 | 11/1990 |

(Continued)

OTHER PUBLICATIONS

International Search Report for PCT/AU2004/001650 dated Feb. 1, 2005.

(Continued)

*Primary Examiner* — Justine Yu  
*Assistant Examiner* — Timothy Stanis  
(74) *Attorney, Agent, or Firm* — Nixon & Vanderhye, P.C.

(57) ABSTRACT

A vent assembly for use with a mask assembly includes a first vent, a second vent and a selector to switch the flow of exhaled gas from a patient between the first and second vents.

45 Claims, 32 Drawing Sheets

(56) References Cited

U.S. PATENT DOCUMENTS

| | | | |
|---|---|---|---|
| 4,207,884 A * | 6/1980 | Isaacson | 128/200.24 |
| 4,437,461 A | 3/1984 | Greenberg | |
| 4,821,713 A * | 4/1989 | Bauman | 128/205.13 |
| 4,919,132 A * | 4/1990 | Miser | 128/205.17 |
| 5,040,532 A * | 8/1991 | Alfery | 128/207.15 |
| 5,067,487 A * | 11/1991 | Bauman | 128/205.13 |
| 5,144,945 A | 9/1992 | Nishino et al. | |
| 5,438,977 A | 8/1995 | Gomez et al. | |
| 5,931,163 A * | 8/1999 | Stegmann et al. | 128/204.26 |
| 6,206,003 B1 * | 3/2001 | Burch | 128/206.21 |
| 6,478,026 B1 | 11/2002 | Wood | |
| 6,536,432 B2 * | 3/2003 | Truschel | 128/205.23 |
| 6,557,555 B1 | 5/2003 | Hollis | |
| 6,561,191 B1 | 5/2003 | Kwok | |
| 6,615,830 B1 * | 9/2003 | Serowski et al. | 128/202.27 |
| 6,629,530 B2 * | 10/2003 | Cise | 128/205.24 |
| 6,662,803 B2 * | 12/2003 | Gradon et al. | 128/205.25 |
| 7,191,781 B2 * | 3/2007 | Wood | 128/206.11 |
| 2003/0005931 A1 | 1/2003 | Jaffre et al. | |
| 2003/0066530 A1 | 4/2003 | Shahbazpour et al. | |

FOREIGN PATENT DOCUMENTS

| | | |
|---|---|---|
| JP | 2001-511035 | 8/2001 |
| JP | 2003/511160 | 3/2003 |
| JP | 2003/190308 | 7/2003 |
| WO | WO 97/28838 A1 | 8/1997 |
| WO | 98/34567 | 8/1998 |
| WO | 98/34665 | 8/1998 |
| WO | WO 02/26287 A2 | 4/2002 |
| WO | 02/051486 A1 | 7/2002 |
| WO | 02/096342 A2 | 12/2002 |

OTHER PUBLICATIONS

Examination Report for Co-Pending Australian Application No. 2004292336, mailed Sep. 23, 2009, 2 pages.
Examination Report for co-pending New Zealand Application No. 586864, mailed Oct. 8, 2010, 2 pages.
Examiner's First Report mailed Apr. 18, 2012 in Australian Appln. No. 2011203068 (3 pages).
Decision of Rejection mailed Apr. 24, 2012 in Japanese Appln. No. 2006-540091, with English translation (5 pages).
Supplementary Search Report for co-pending European Application No. 04797092.6, mailed Aug. 27, 2010.
Examination Report mailed Dec. 9, 2011 in New Zealand Appln. No. 586864 (3 pages).
Office Action issued in JP 2006-540091, mailed Jun. 1, 2010 with English translation.
Office Action issued in JP 2006-540091, mailed Apr. 19, 2011, with English translation.
Notification of Fourth Office Action mailed Dec. 21, 2011 in Chinese Appln. No. 200480034866.9.
New Zealand Examination Report mailed Nov. 16, 2011 in New Zealand Appln. No. 596356 (2 pages).

* cited by examiner

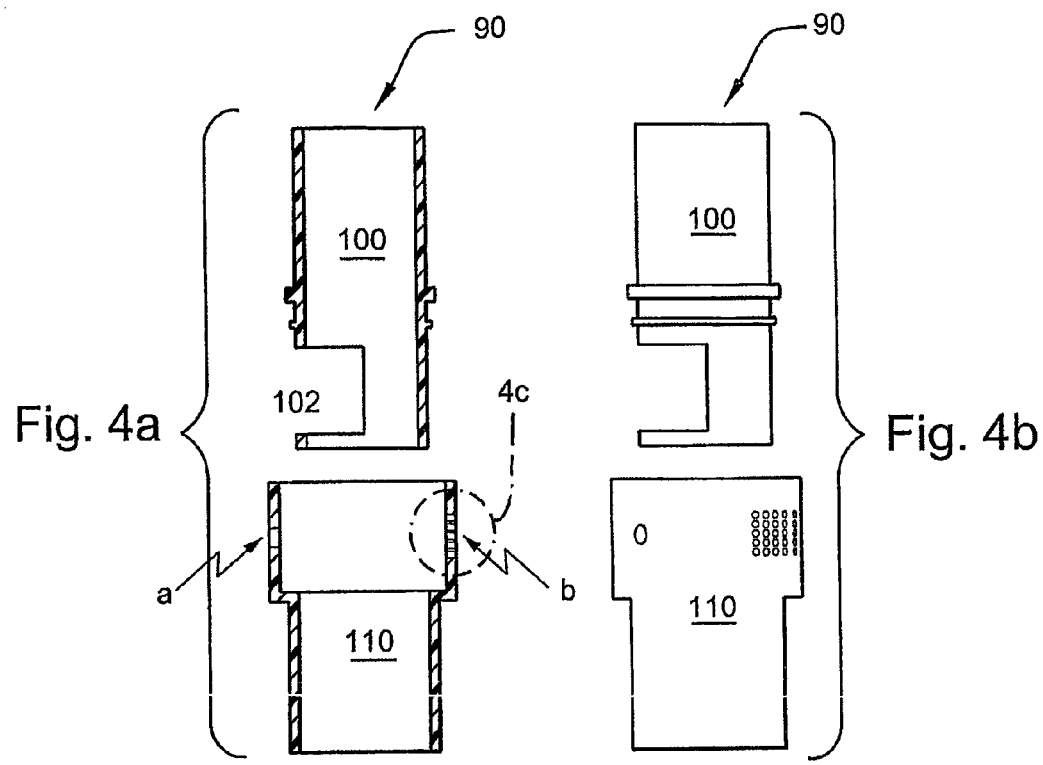
Fig. 4a
Fig. 4b
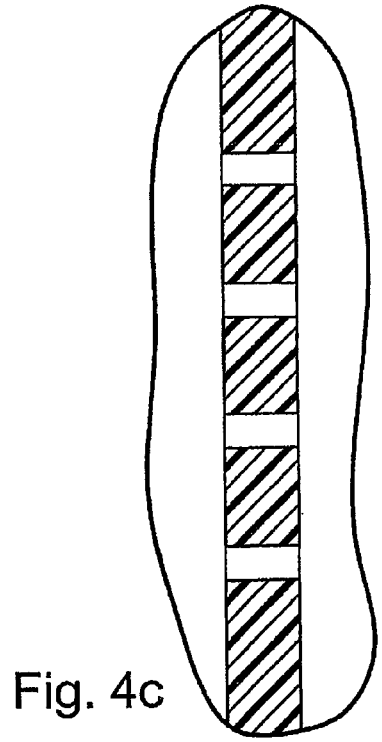
Fig. 4c

VENT SYSTEM FOR CPAP PATIENT INTERFACE USED IN TREATMENT OF SLEEP DISORDERED BREATHING

CROSS REFERENCE TO PRIORITY APPLICATIONS

This application is the US national phase of international application number PCT/AU2004/001650 filed 25 Nov. 2004, which designated the U.S. and claims priority to U.S. Provisional Application No. 60/524,728 filed 25 Nov. 2003, U.S. Provisional Application No. 60/538,507 filed 26 Jan. 2004, and U.S. Provisional Application No. 60/550,319 filed 8 Mar. 2004, the entire contents of each of which are hereby incorporated by reference.

FIELD OF THE INVENTION

The invention relates to a vent system for use with a Continuous Positive Airway Pressure (CPAP) patient interface, e.g. a mask, used in treatment of Sleep Disordered Breathing.

BACKGROUND

The use of nasal CPAP apparatus to treat "snoring sickness" was pioneered by Sullivan and taught in U.S. Pat. No. 4,944,310. Nasal CPAP apparatus typically comprises a blower, an air delivery conduit and a patient interface. The blower provides a supply of air or breathable gas at positive pressure. The conduit interconnects the blower and the patient interface. A variety of nasal masks, nose & mouth masks, full face masks, nasal prongs and nasal pillows are used to provide an interface with the patient.

A typical mask comprises;
(i) a rigid or semi-rigid portion, termed a shell or frame, which defines a nose-receiving cavity; and
(ii) a soft patient contacting portion, termed a cushion or membrane.
Cushions have been constructed from silicone, foam, gel and combinations of these materials.

Since a patient typically exhales into the same mask cavity wherefrom they inhale, the possibility of rebreathing of carbon dioxide ($CO_2$) exists. In conjunction with a sufficient continuous flow of fresh air or breathable gas, a vent can allow a controlled leak from the mask cavity and hence provide for the washout of $CO_2$. Unfortunately, the noise of air or breathable gas from the vent can disrupt anyone within earshot attempting to sleep. Hence there is an advantage in providing a low-noise vent.

One form of known vent is described in U.S. Pat. Nos. 6,561,190 (Kwok) and 6,561,191 (Kwok). These patents describe the use of grommet in a mask frame. The contents of these patents are hereby incorporated by cross-reference. A vent in accordance with embodiments of these inventions is found in the MI/RAGE™ mask, manufactured by ResMed Limited.

Another known form of vent is described in International Patent Application PCT/AU00/00636 (Drew et al.) published as WO 00/78381. This patent application describes the use of a connector for a mask having a vent along a smooth continuing surface. The contents of this patent application are hereby incorporated by cross-reference. A vent in accordance with an embodiment of this invention is found in the ULTRA MIRAGE™ mask, manufactured by ResMed Limited.

Another known form of vent is described in U.S. Pat. No. 6,581,594 (Drew et al.). This patent describes the use of a vent which, in one form, comprises a thin air permeable membrane. The contents of this patent application are hereby incorporated by cross-reference.

Another known form of vent is described in International Patent Application PCT/AU01/01658 (Dantanarayana et al.) published as WO 02/051486. This patent application describes the use of a flow regulation vent. The contents of this patent application are hereby incorporated by cross-reference.

U.S. Pat. No. 6,557,555 (Hollis) describes a vent valve apparatus. The contents of this patent application are hereby incorporated by cross-reference.

Another known vent is the Respironics WHISPER swivel.

European Patent No. 0 697 225 discloses a vent formed from a porous sintered material.

A known vent, manufactured by Gottleib Weinmann Geräte Für Medizin Und Arbeitsschutz GmbH and Co. comprises a generally cylindrical insert to be interposed in use, between the mask shell and the gas conduit. The insert includes a window which is covered with a porous sintered material of approximately 3-4 mm thickness.

Another type of vent intended to be inserted between the mask shell and the breathable gas supply conduit is the E-Vent N by Draeger medizintechnik GmbH (the Draeger vent). The Draeger vent comprises a stack of 21 annular disks, which have slots in their adjacent surfaces for gas to flow therethrough. Each slot has a length of 5 to 7 mm as measured along the path from the interior of the vent to atmosphere.

Typically vents are designed with sufficient porosity to provide enough vent flow at a low pressure (e.g. 4 cm $H_2O$) to ensure adequate washout of $CO_2$.

Reducing the pore size of a vent can make the vent quieter, but can also increase the chances that the vent will clog.

Problems with prior art vents include that they can be too noisy, that they clog with dirt and moisture (particularly when used with humidifiers), that they are awkward or difficult to clean or assemble and that they have designs which are sensitive to very small changes in the manufacturing process which can lead to variation in the pressure flow relationship.

SUMMARY OF THE INVENTION

In accordance with a first aspect of the invention there is provided a vent for a CPAP patient interface.

In accordance with a second aspect of the invention there is provided a vent assembly comprising at least two alternative vents each having substantially the same pressure-flow characteristics.

In accordance with a third aspect of the invention there is provided a vent assembly comprising at least two alternative vents each having different pressure-flow characteristics.

In accordance with another aspect of the invention there is provided a vent assembly comprising at least two alternative vents and a mount adapted to support at least one vent in a venting position.

In accordance with another aspect of the invention there is provided a vent assembly comprising at least two alternative vents and a mount adapted to support at least one vent in a venting position and a locking mechanism adapted to retain said at least one vent in a venting position.

In accordance with still another aspect, there is provided a mask assembly for a patient comprising a frame, a cushion provided to the frame, and a vent assembly including a first vent, a second vent, and a selector to switch the flow of exhaled gas from the patient between the first and second vents.

BRIEF DESCRIPTION OF THE DRAWINGS

FIG. 4a-c show side views, a cross section and a detail of a swivel in accordance with a first embodiment of the invention.

FIG. 12 shows a further view of the vent assembly of FIG. 11a.

FIG. 13 shows a drawing of the vent assembly of FIG. 11a.

FIG. 14 shows an alternative view of the vent assembly of FIG. 11a.

DETAILED DESCRIPTION OF PREFERRED EMBODIMENTS

Figure 1:
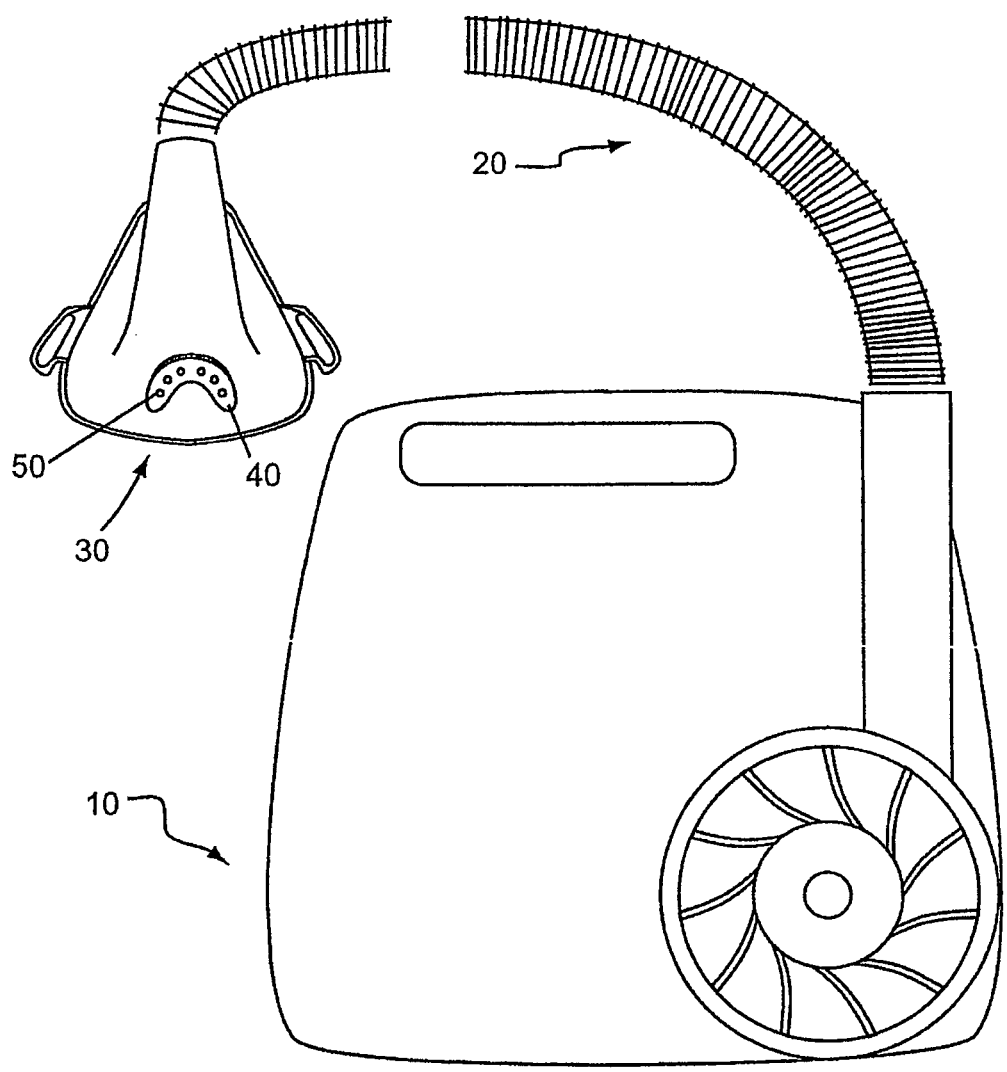
FIG. 1 shows a schematic diagram of a prior art blower, air delivery conduit and patient interface.

FIG. 1 shows a blower 10 connected to an air delivery conduit 20 and the air delivery conduit 20 connected to a patient interface 30. In the view shown in FIG. 1, the patient interface 30 is a nasal mask. The patient interface 30 includes a vent 40. The vent 40 includes one or more holes, e.g., six holes 50.

Figure 2:
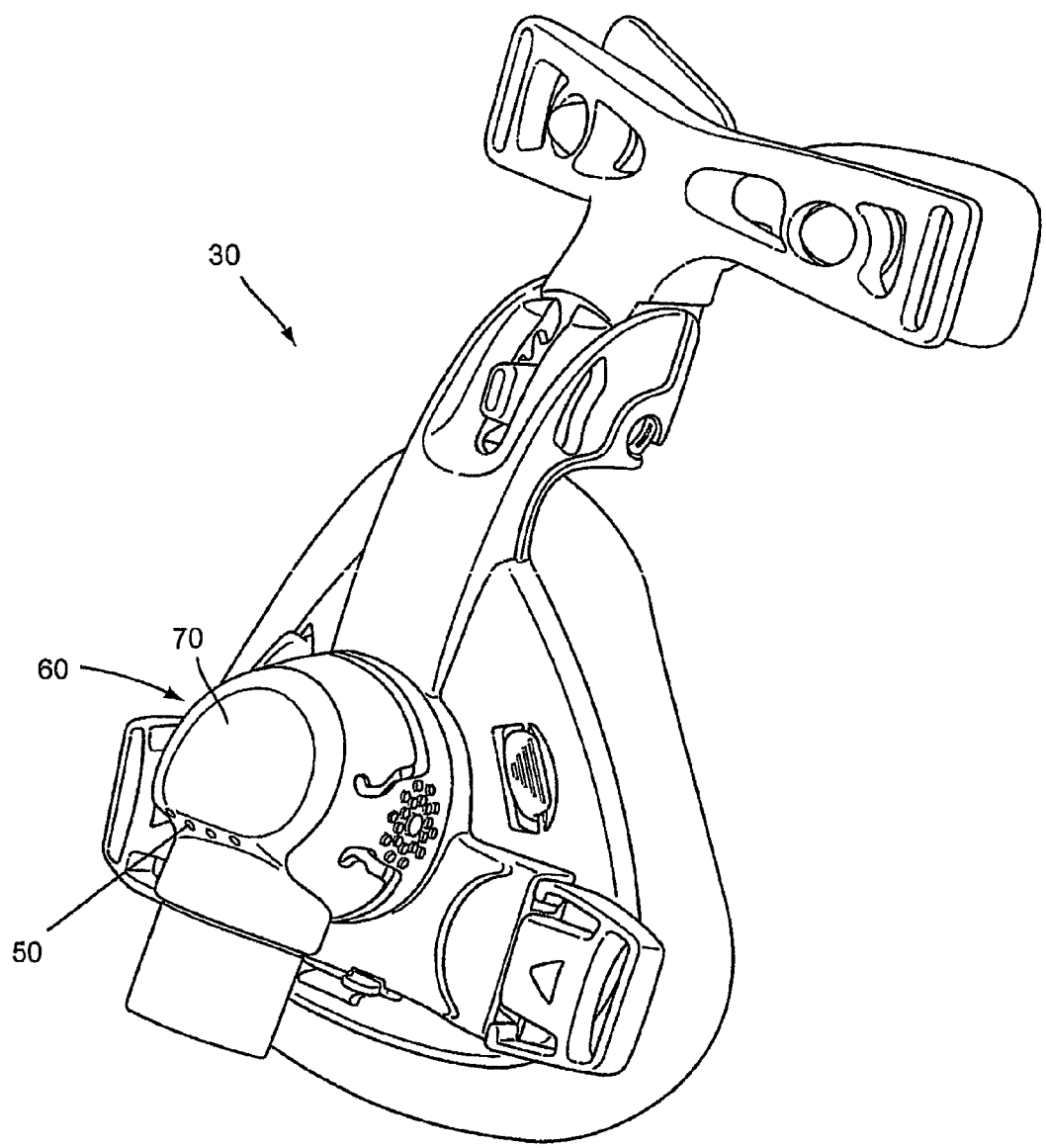
FIG. 2 shows a related art mask with swivel elbow.

FIG. 2 shows an alternative nasal mask, the MIRAGE® ACTIVA™ nasal mask. This mask includes a swivel elbow 60. The swivel elbow is described in further detail in the Applicant's co-pending International Patent Application PCT/AU03/01162, the contents of which are hereby incorporated by cross-reference. The swivel elbow 60 includes a vent cover 70 having a number of holes 50 therethrough.

Figure 3:
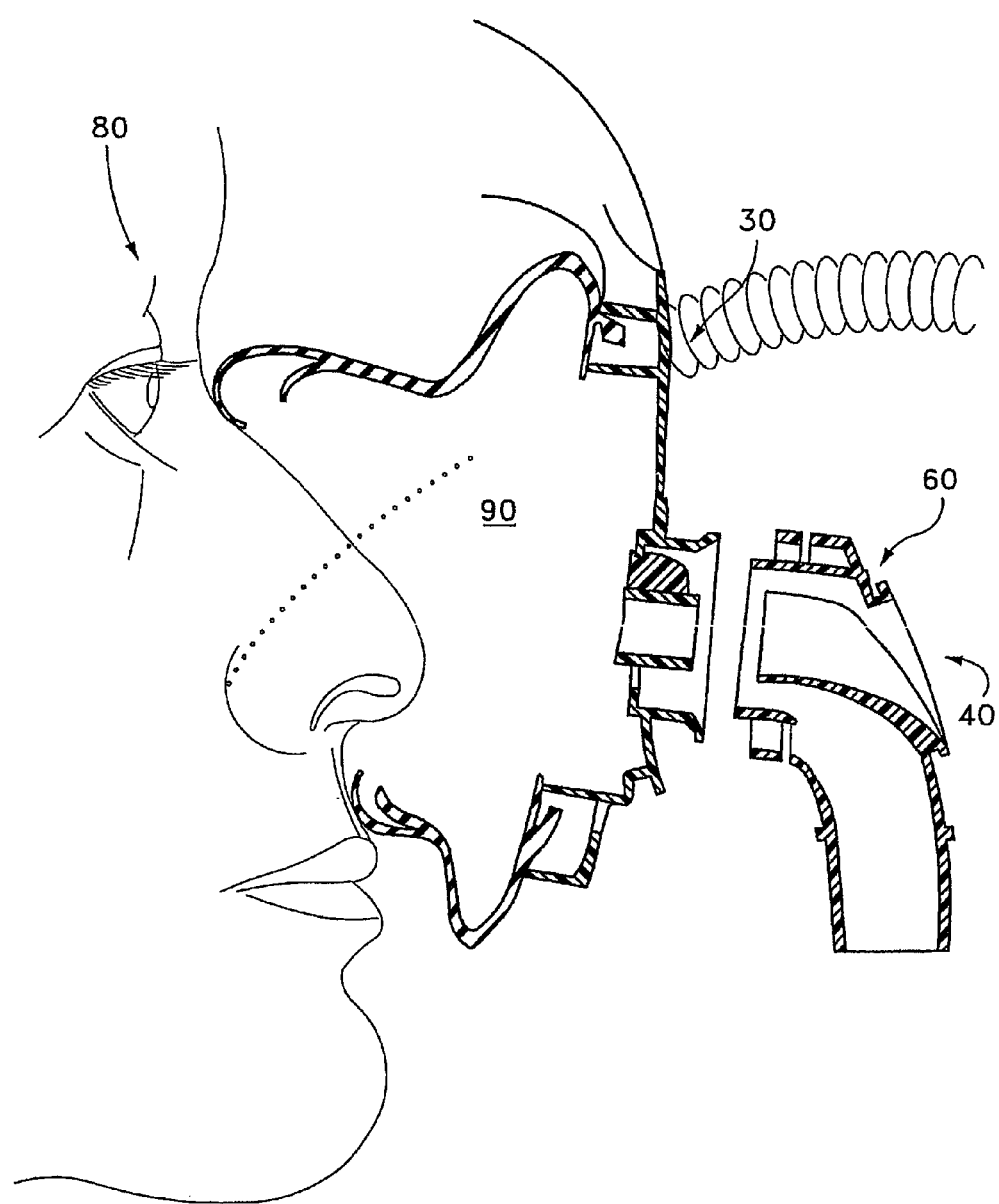
FIG. 3 shows a cross-section of a related art patient interface in position on a patient's face with swivel elbow.
Figures 5A, 5B, 5C:
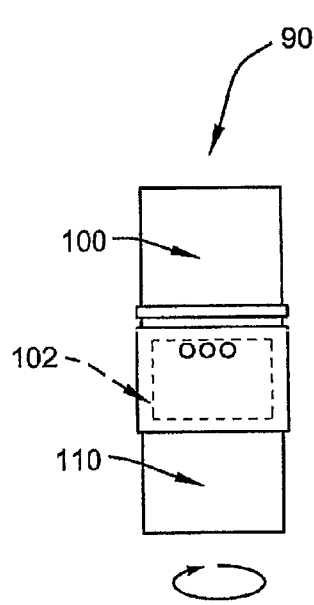
FIG. 5a-c shows a swivel in accordance with a first embodiment of the invention in three positions.
Figure 6:
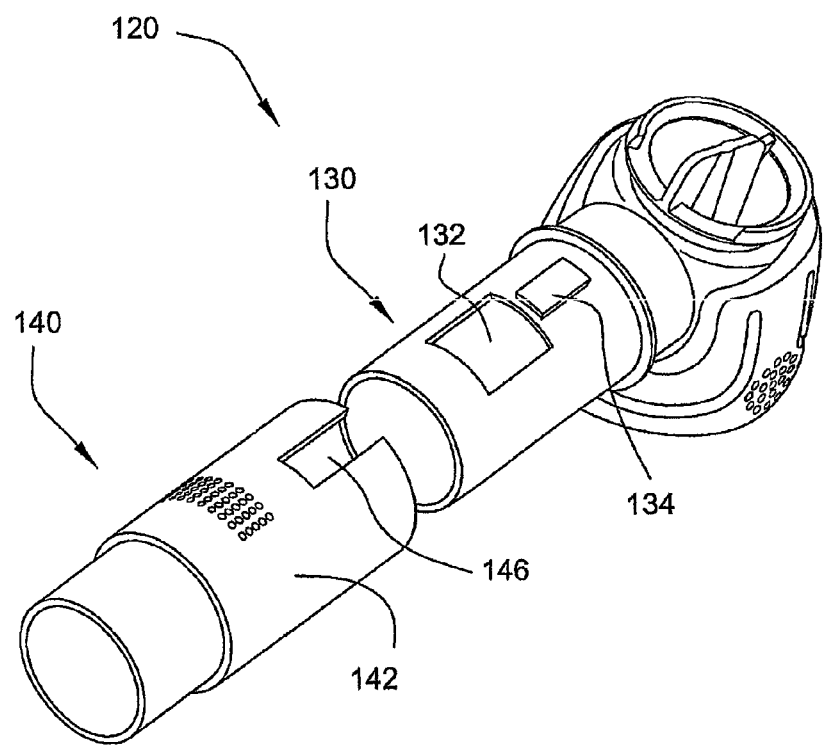
FIG. 6 shows an exploded perspective view of a swivel elbow in accordance with a second embodiment of the invention.

FIG. 3 shows a cross-section of a patient interface 30 in position on a face of a patient 80. A swivel elbow 60 is shown detached and in front of the patient interface 30. The cavity 90 into which the patient 80 can exhale nasally can accumulate carbon dioxide unless it is washed out through the vent 40 included in the elbow 60.

In a first embodiment of the invention, a vent assembly is provided with two alternative vents, vent a and vent b as shown in FIG. 4a-5c. Both vent a and vent b provide approximately the same total flow. Vent a provides relatively fewer large vent holes, whereas vent b provides a matrix of relatively smaller holes (e.g. below 0.5 mm diameter, preferably approximately 0.1 mm in diameter). Selection between vent a and vent b is made by rotating or sliding a cover so that either the small or large holes are lined up with an orifice on a mating surface.

As shown in FIGS. 4a and 4b in exploded views, a vent assembly 90 in accordance with an embodiment of the invention comprises a generally cylindrical first portion 100 and a generally cylindrical sleeve portion 110. The first portion 100 includes an orifice or window 102. The sleeve portion 110 includes, in one embodiment, two alternative sets of holes corresponding to vents a and b respectively. Vent a uses three large holes. Vent b uses a series of smaller holes. In use the sleeve portion 110 rotatingly fits over an end of the first portion 100. In the embodiment of the invention shown in FIG. 4a, the sleeve is free to rotate through 180° degrees as shown by the arrows in FIG. 5a-5c, although in other embodiments the sleeve may rotate through fewer degrees. As shown in FIG. 4a-4b, both the first portion 100 and sleeve portion 110 are hollow which allows air to pass between the interior of the first portion 100 through window 102 and thence through either of vent holes a or b. FIG. 4c shows a detail of the vent with small holes.

In a second embodiment of the invention the vent assembly is formed as part of a swivel elbow 120, for example, the swivel elbow used on the MIRAGE® VISTA™ mask, manufactured by ResMed Limited, as shown in FIG. 6-9. The elbow 120 includes a shaft 130 with an orifice 132 therein. The shaft 130 includes an alignment tab 134. A sleeve 140 includes a pair of alternative vents 142, 144 and a pair of slots 146, 148, each one associated with one vent, each adapted to receive the alignment tab of the shaft. In use, the orifice 132 of the shaft 130 aligns with either vent 142 or vent 144. In order to change from one vent to another, the vent assembly is pulled apart, rotated 180°, and re-assembled. In this way, at least one of and only one of vents 142 or 144 is used at one time.

In a third embodiment of the invention the vent assembly includes a moving part. The moving part can be located in each of two positions by having a protrusion on one part match a depression on the matching part. Alternatively, the two positions can simply be defined by use of appropriate positioning structure, e.g., detents, ratchets, etc. When the vent assembly is partway between the two vent positions, the protrusion can act to separate the matching parts so that the vented airflow is greater than in either of the two correct positions. This provides a fail-safe mechanism where an incorrect position results in high airflow (a safe condition) and also higher noise (warning the user of the mistake). Generally speaking, the assembly can be configured such that a warning, e.g., a noise, can be created when the vent parts are misaligned.

A typical vent comprises a number of vent holes. For example, three vent holes with a diameter of 2.7 mm. The effective area of a vent hole is generally smaller than the actual cross-sectional area of the vent hole. Small holes have a relatively smaller effective area than large holes, e.g. about 10% smaller. The effective area of a vent is the sum of effective areas of its constituent vent holes. In one form the alternative vents have the same effective areas.

In another embodiment of the invention, alternative vent constructions are used instead of using holes. For example, vent a and vent b are laminar flow elements, such as used in the ULTRA MIRAGE® mask. In another form sintered materials are used to construct the vent. In another form, vents are constructed from foam polymers. Combinations of different vents may be used, for example, a vent with holes and a vent constructed from a sintered material. The assembly may comprise more than two vents, for example a vent with holes, a sintered vent and a laminar flow element-type vent.

In some cases, such as clinical studies, it is desirable to test the effectiveness of a particular treatment regime, or mask and compare it with a suitable control. For example, it might be desired to test the effectiveness of an algorithm for providing nasal CPAP therapy. In such a situation, it would be desirable to be able to discount the effect of wearing the mask per se. This could be achieved by using a "sham" mask, for example, a mask with a very large vent hole. An example of a sham mask is taught in published PCT patent application WO 02/066,105. A difficulty of using a dedicated "sham" mask is that the patient may be aware that they are using the sham mask, or that it may be necessary to disturb their sleep in order to don such a sham mask.

The vent assembly may include a sham vent as an alternative. Such a sham vent would have a very high permeability, e.g. a large hole. By use of the invention, it would be possible for a clinician to switch from a "treatment" vent to a "sham" vent, with minimal disturbance to a sleeping patient and thus obtain clearer results for a clinical study.

Whilst in a preferred form the different vents are alternatives, in one form more than one vent may be used at once, for example, ½ vent a and ½ vent b.

In a vent comprising vent holes, increasing or decreasing the number of holes in the vent allows the vent flow to be set to any desired level. In this way a vent assembly in accordance with the invention can be designed to have pressure flow characteristics that mimic prior art masks which use vents with holes.

A variety of materials may be used to construct the vent assembly, for example, polycarbonate (e.g. MAKROLON), or other polymers, stainless steel, sintered ceramic or PTFE, and foam polymers. It may be particularly advantageous to use hydrophobic materials such as PTFE for small pored vents to reduce clogging of pores.

Figure 11A:
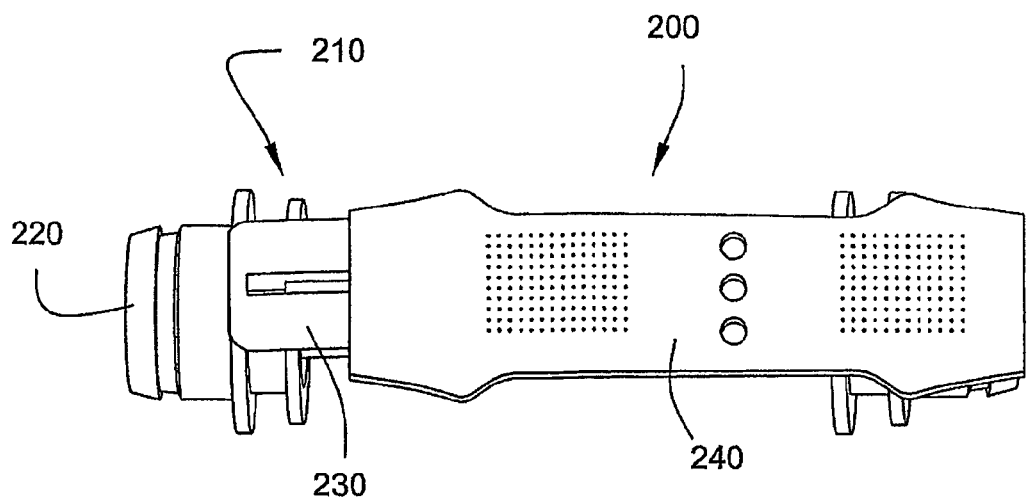
FIGS. 11a and 11b show a sliding vent assembly in accordance with an embodiment of the invention.
Figure 11B:
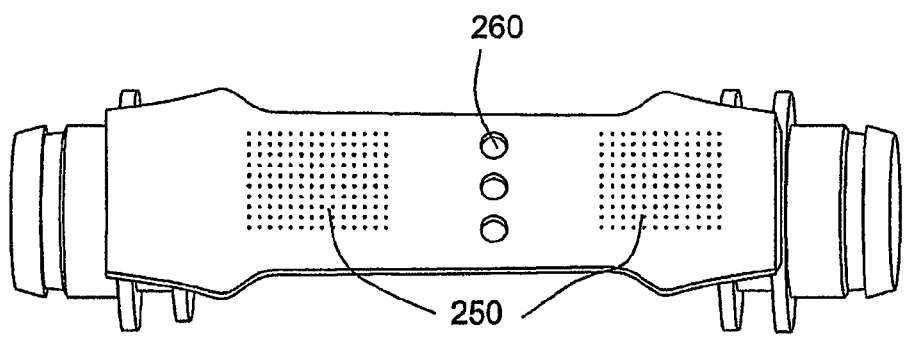
Figure 12:
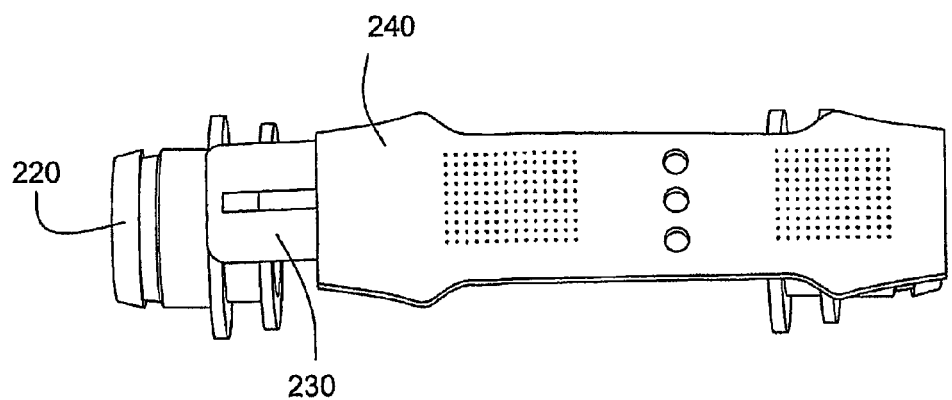
Figure 13:
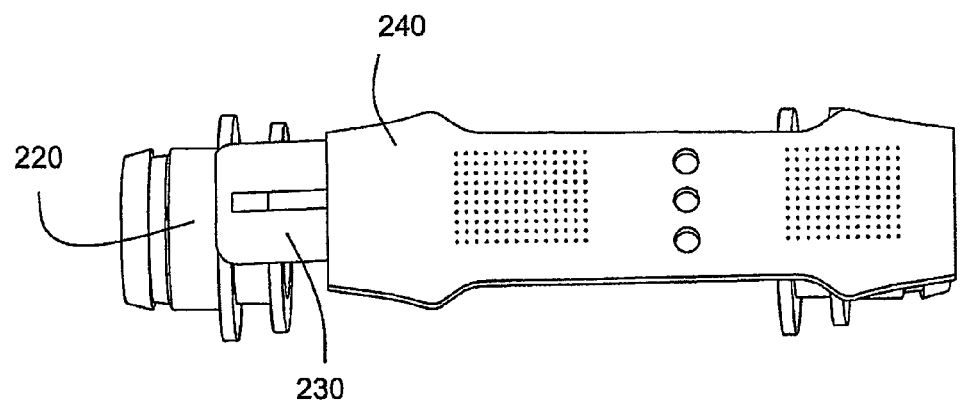
Figure 14:
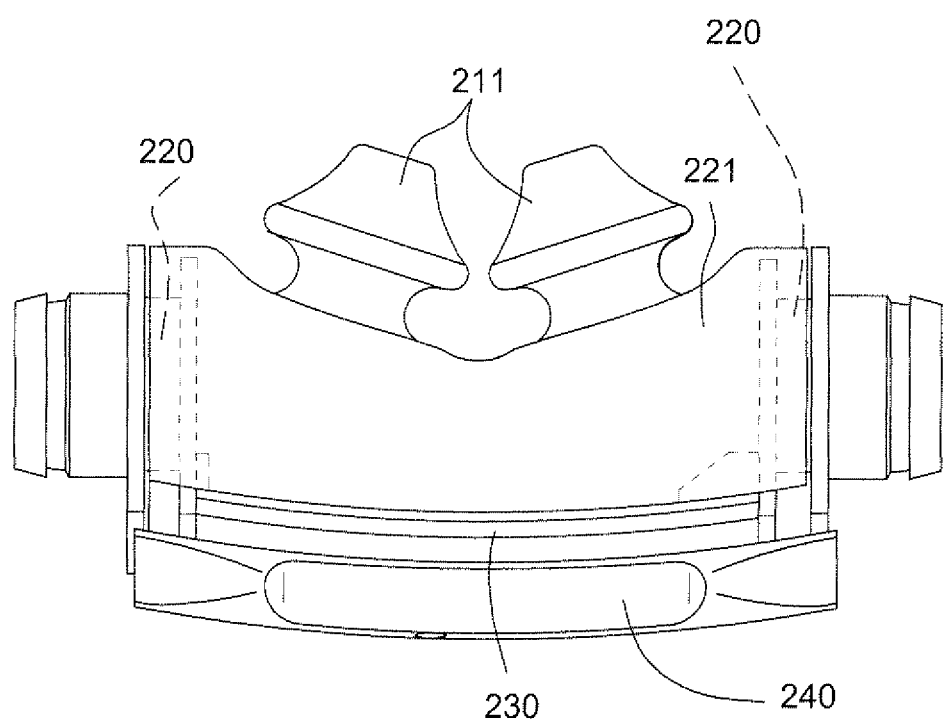
Figure 15:
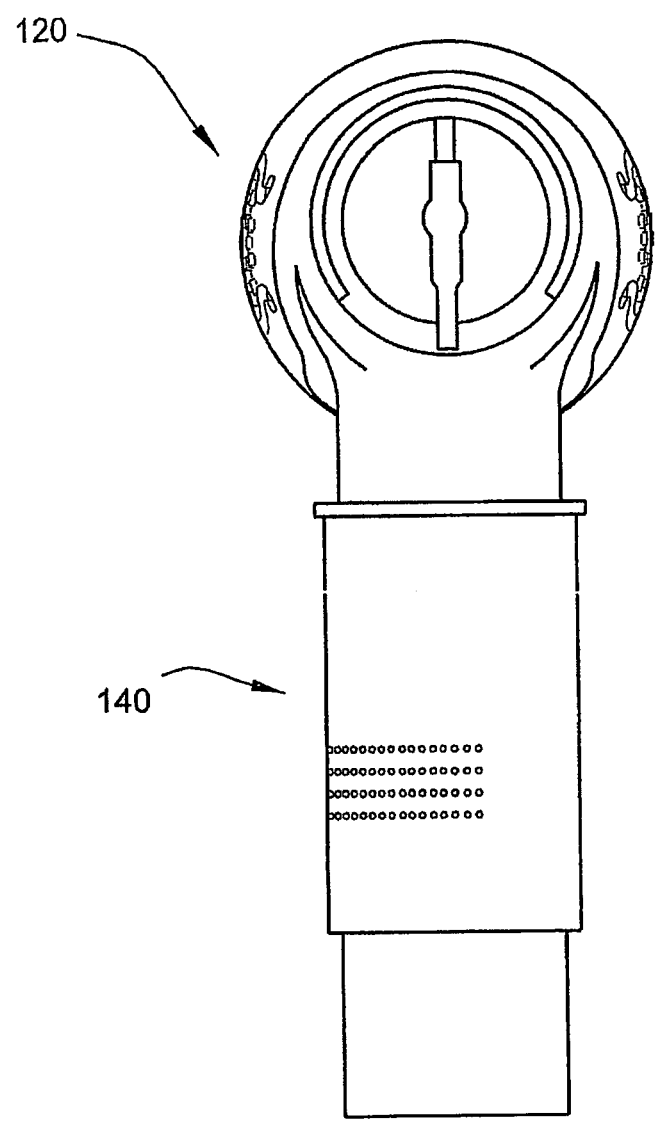
FIG. 15 shows a front view of a swivel elbow with vent assembly in accordance with a first embodiment of the invention.
Figure 16:
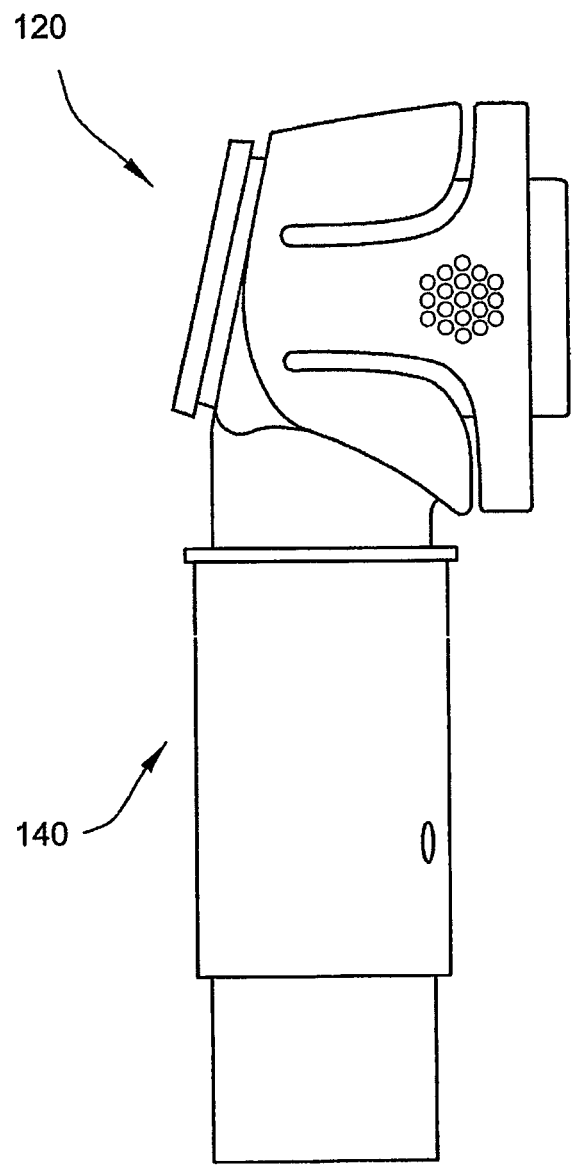
FIG. 16 shows a side view of a swivel elbow with vent assembly in accordance with a first embodiment of the invention.
Figure 17:
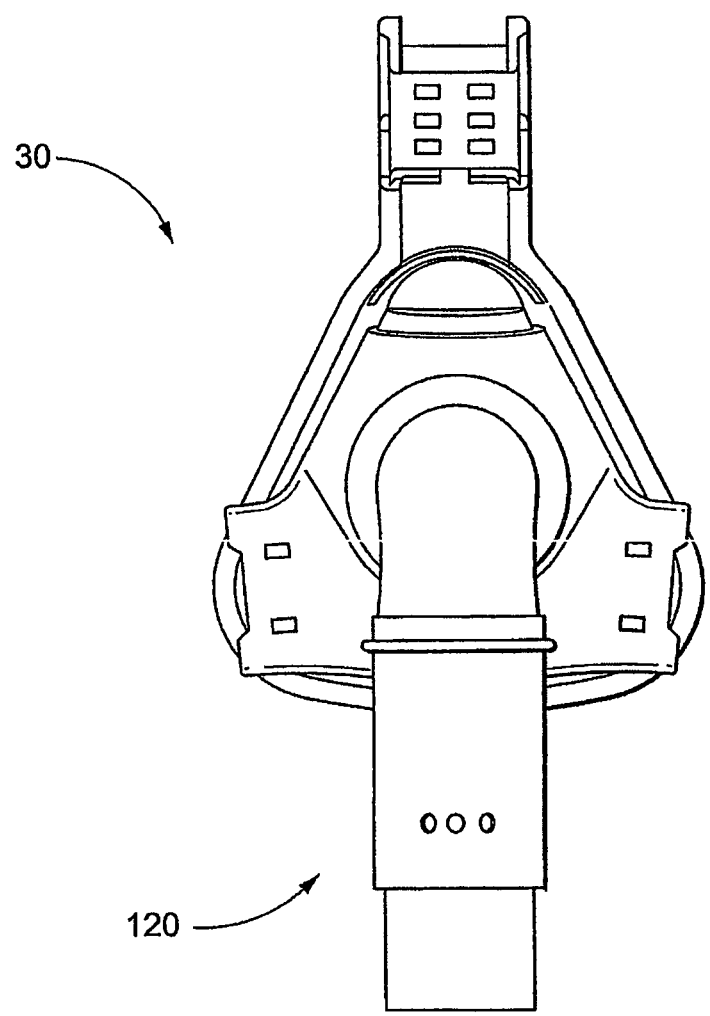
FIG. 17 shows a front view of an assembly including mask frame and swivel elbow with vent assembly in accordance with a first embodiment of the invention.
Figure 18:
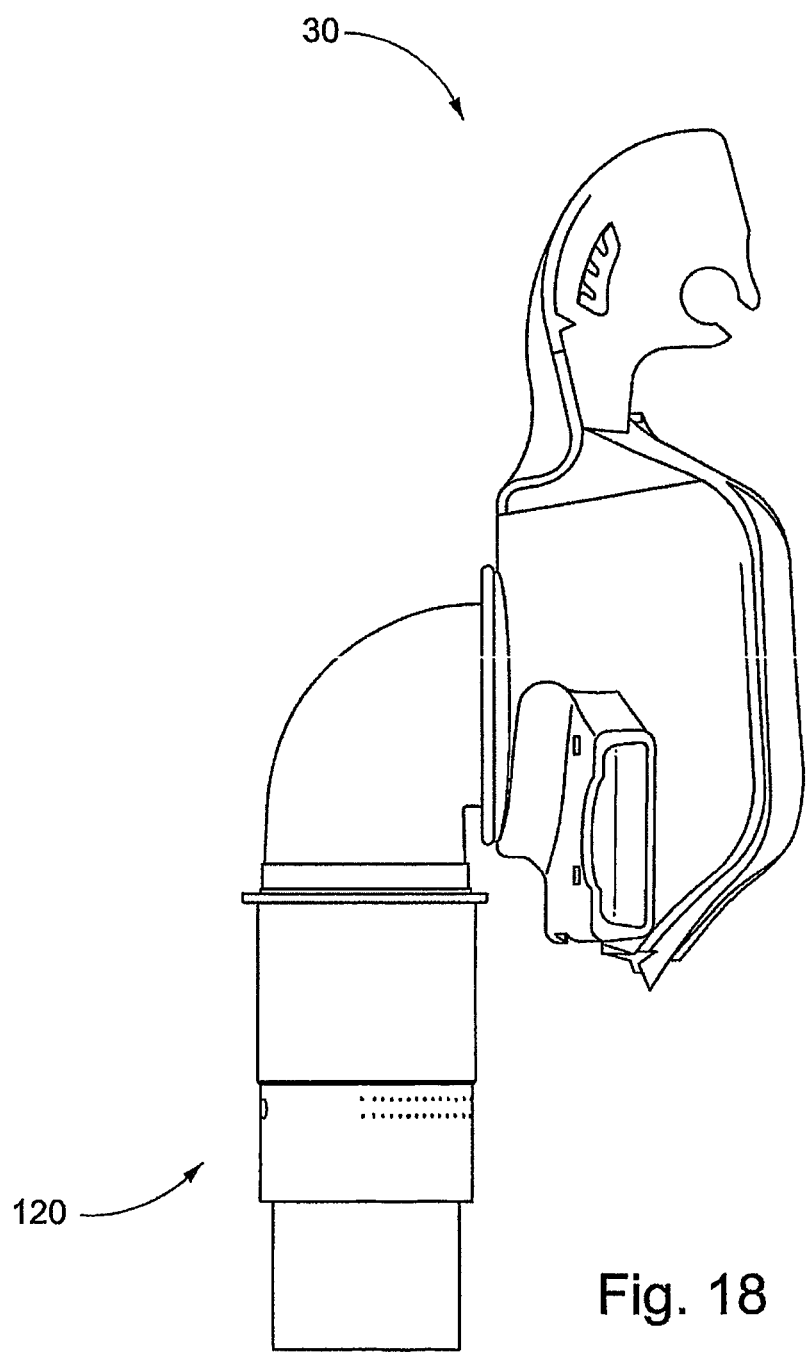
FIG. 18 shows a side view of the assembly of FIG. 17.
Figure 19:
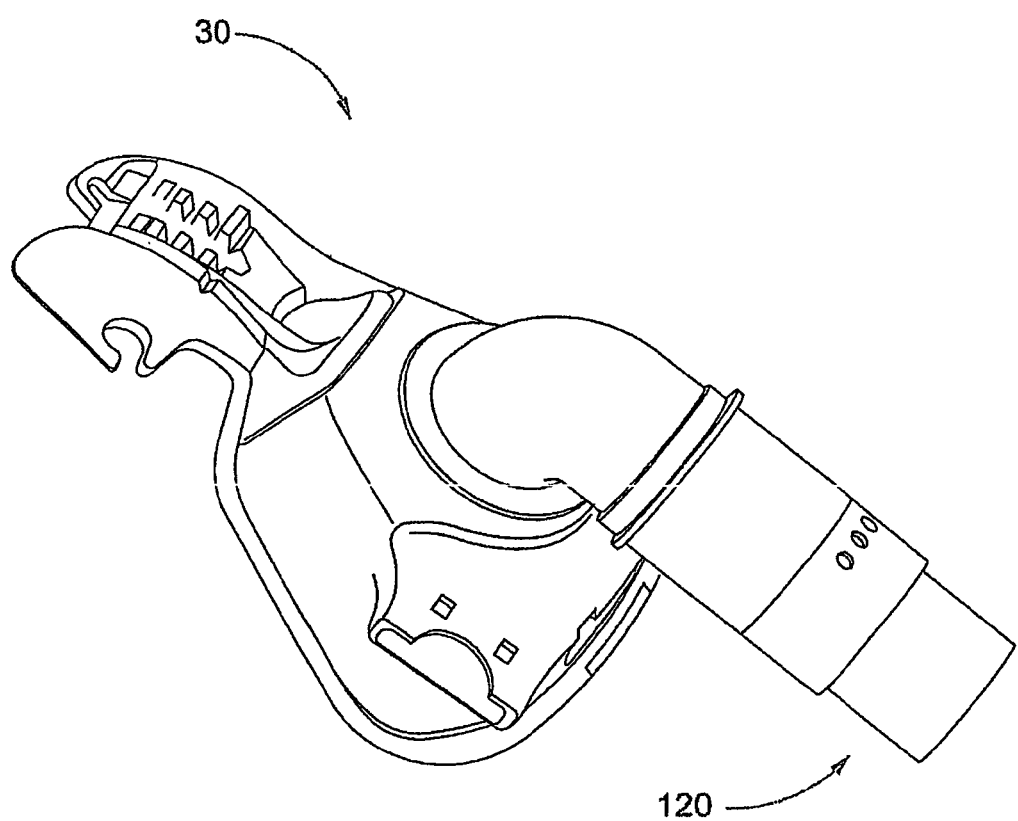
FIG. 19 shows a perspective view of the assembly of FIG. 17.

In an alternative form, instead of being mounted on a swivel elbow, a vent assembly 200 in accordance with an embodiment of the invention is mounted on or formed as part of a patient interface frame 210. FIGS. 11a-14 show a frame for a patient interface which comprises two generally cylindrical end portions 220 interconnected by a generally rectangular backbone 230. Nozzles 211 may be included to interface with the nostrils of a user. A clip 240 is slidably positioned on the backbone 230. The clip 240 includes at least two alternative vents 250, 260. One or more orifices or windows in the backbone 230, similar to orifice or window 102, provides for fluid communication to an interior of the patient interface. By sliding the clip 240 to alternatively align vent 250 or 260 with the orifice, exhaled air can be vented via vent 250 or 260. FIG. 11a shows the clip 240 in a first position in which the vent 260 is aligned with an orifice in the backbone, and one or both vents 250 are sealed. FIG. 11b shows the clip 240 in a second position in which one or both vents 250 are aligned with respective orifices in the backbone, and the vent 260 is sealed.

Figure 22:
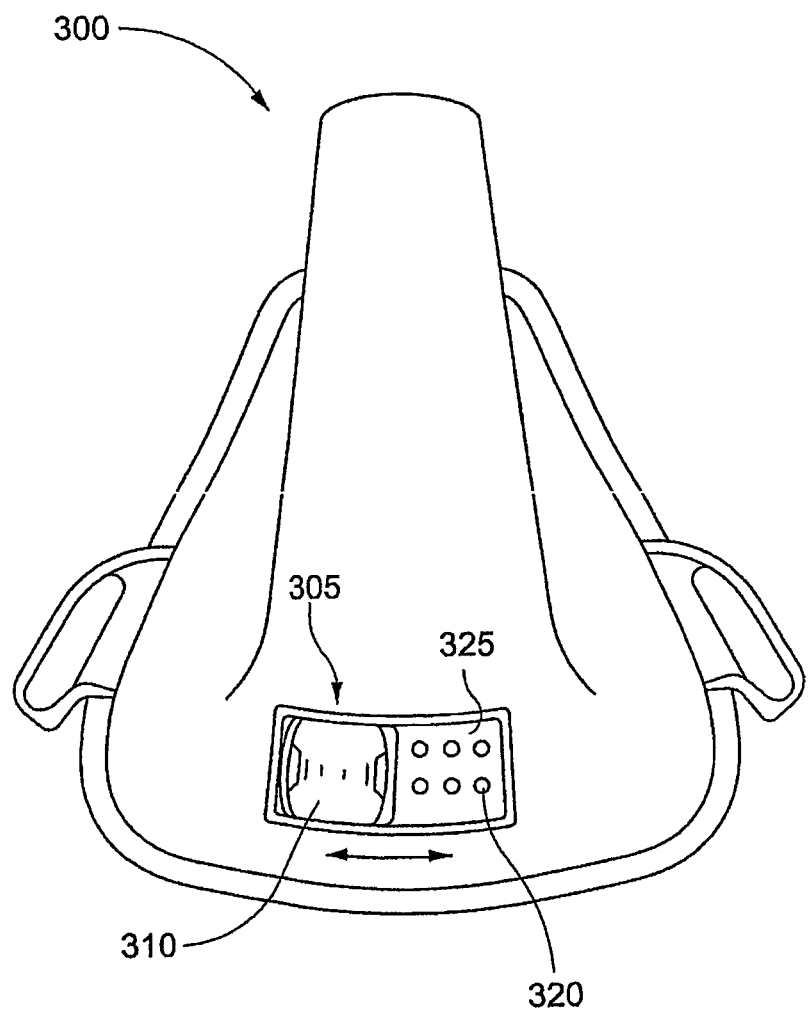
FIG. 22 shows an embodiment of the invention with a slidable vent cover exposing a set of larger holes.
Figure 23:
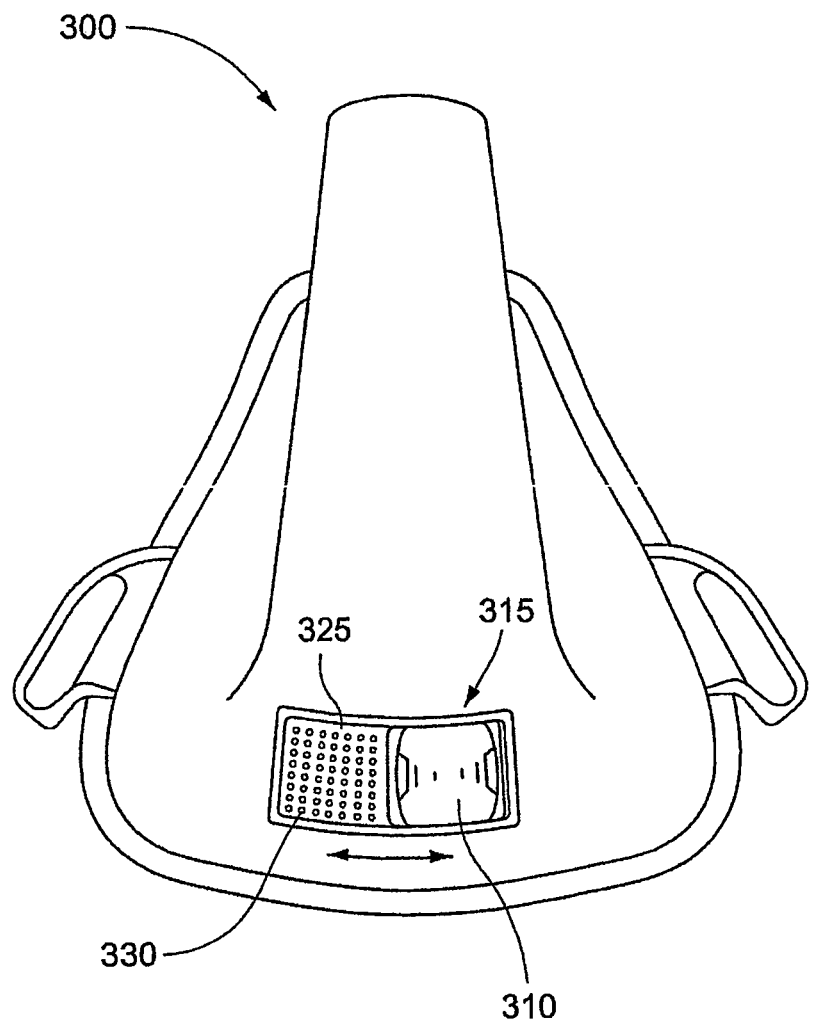
FIG. 23 shows an embodiment of the invention with a slidable vent cover exposing a set of smaller holes.

FIGS. 22 and 23 show an alternative embodiment of the invention in a nasal mask 300. This form of the invention includes a slidable vent cover 310 which in a first position 305 exposes a set of large vent holes 320 and in a second position 315 exposes a set of small vent holes 330. In one form the large and small vent holes are molded into a silicone grommet 325 which is removably insertable into a mask frame, in a similar manner to U.S. Pat. Nos. 6,561,190 and 6,561,191 (Kwok). When holes are exposed the passage of air between the interior of the mask and the exterior of the mask can occur therethrough.

Figure 23A:
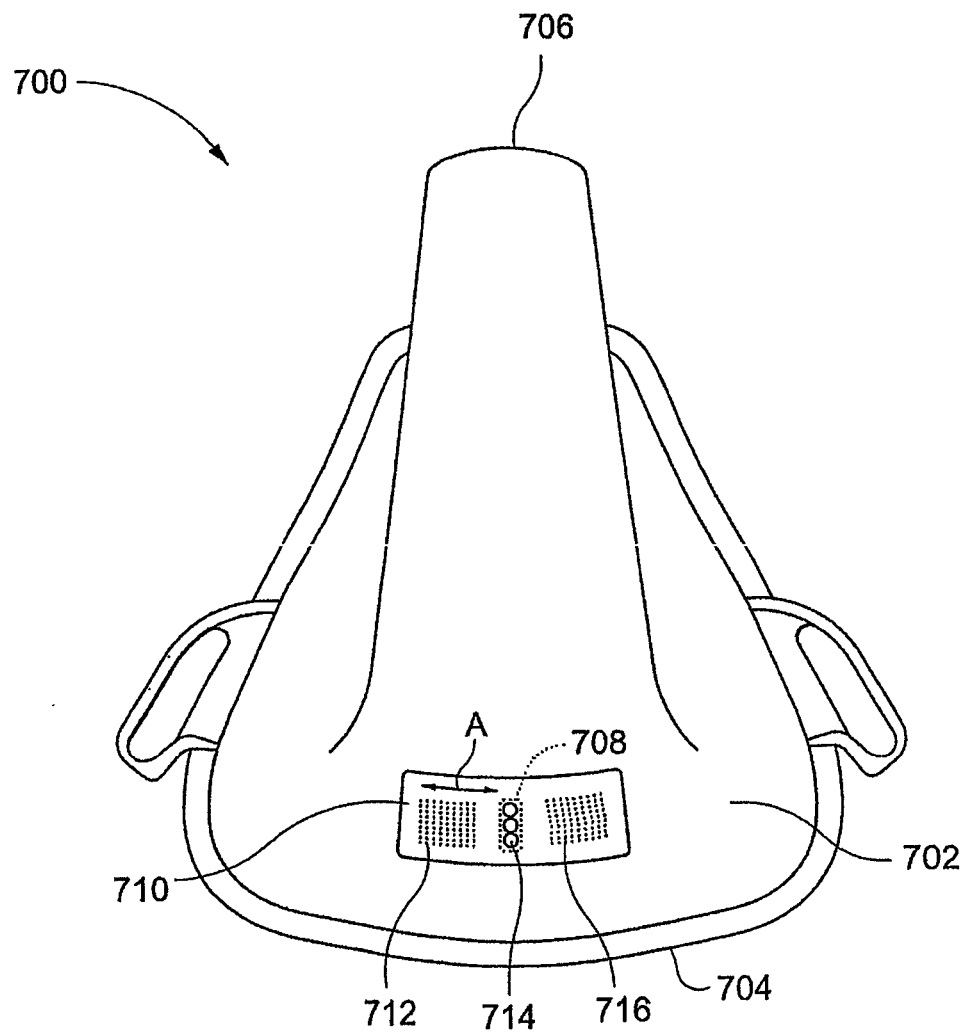
FIGS. 23a-23c illustrate still another embodiment of the present invention.

FIG. 23a illustrates another embodiment of the present invention having a mask assembly 700 with a shell 702 and a cushion attached or otherwise provided to the shell 702. The shell 702 includes an aperture 706 by which pressurized breathable gas is provided to an interior chamber defined by the shell 702 end cushion. Alternatively, a swivel elbow may be provided to a frontal aperture of the shell 702, in which case the elbow would include a conduit that delivers breathable gas from a source to the frontal aperture.

Figure 23B:
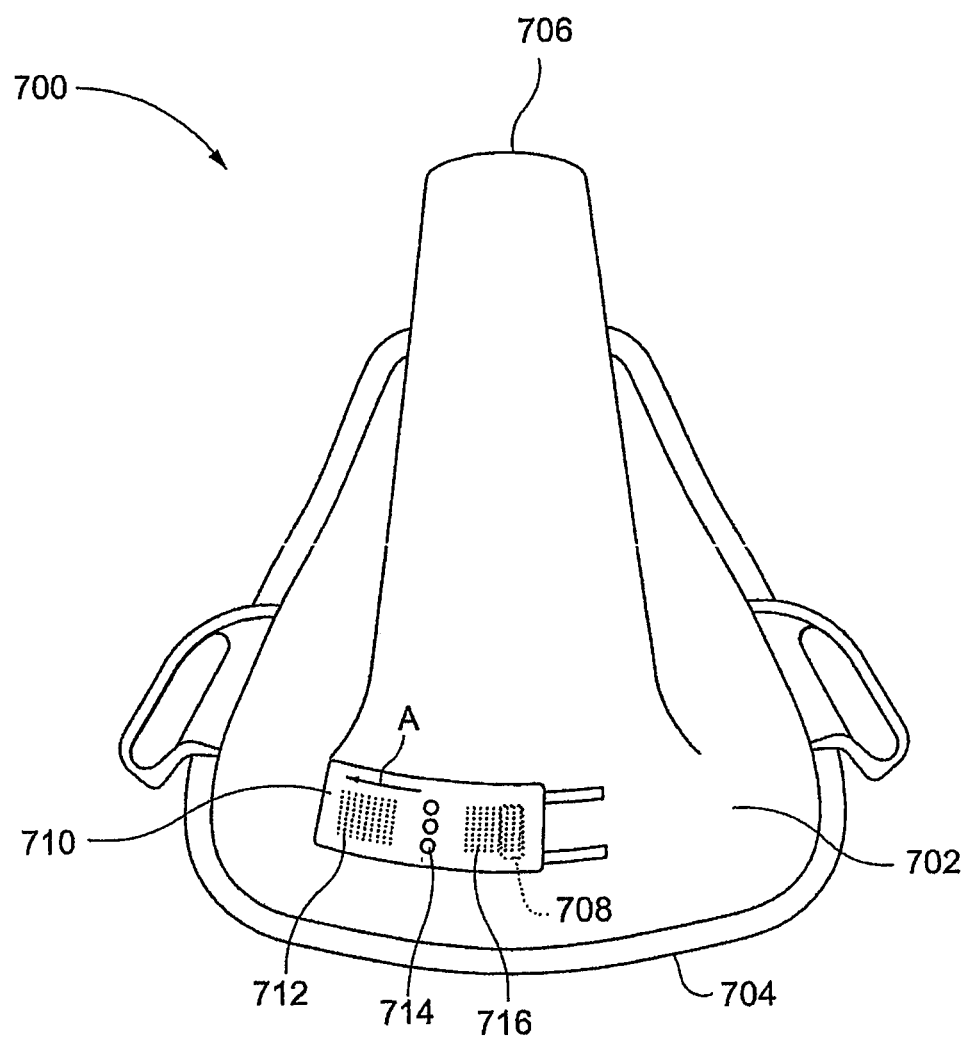

The shell 702 includes at least one aperture 708, in this case formed in a rectangular shape to make it easily visible. The aperture 708 is structured to continuously vent $CO_2$ during administration of CPAP or NIPPV therapy, for example. A slidable vent plate 710 includes first, second and third aperture portions 712, 714, 716 that may be selectively aligned (via sliding along the direction of arrows A) with the aperture 708. As shown in FIG. 23a, the second aperture portion 714 is aligned with shell aperture 708, while FIG. 23b shows the plate 710 in a shifted position in which third aperture portion 716 is aligned with shell aperture 708. Therefore, the clinician or patient may change the venting characteristics of the mask.

Figure 23C:
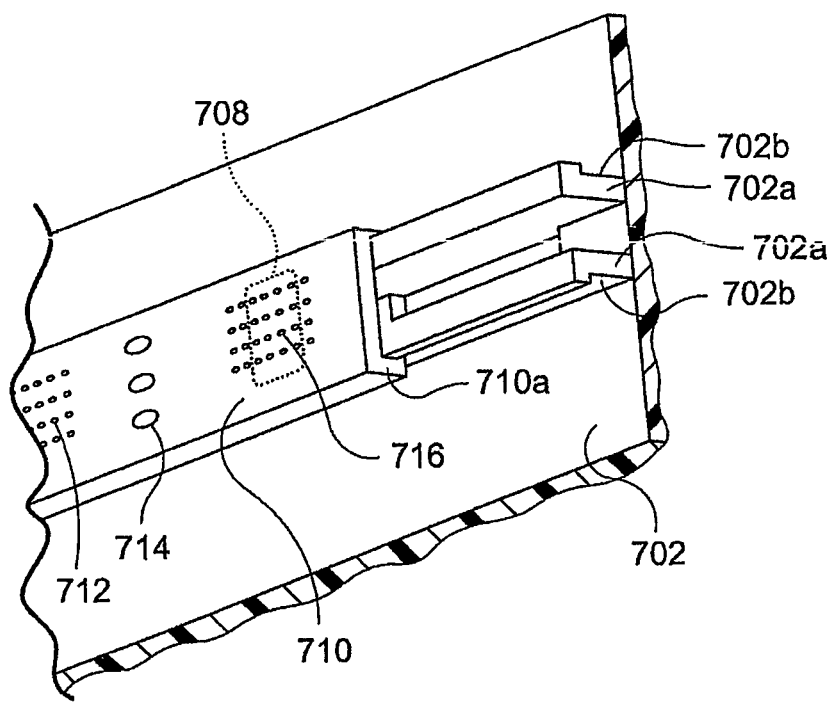

As shown in FIG. 23c, a partial schematic cross-section of FIG. 23a, the vent plate 710 may be releasably held by the shell 702. For example, the shell 702 may include a pair of legs 702a each forming a groove 702b with which a leg portion 710a of the plate 710 may slidingly engage.

Figure 24:
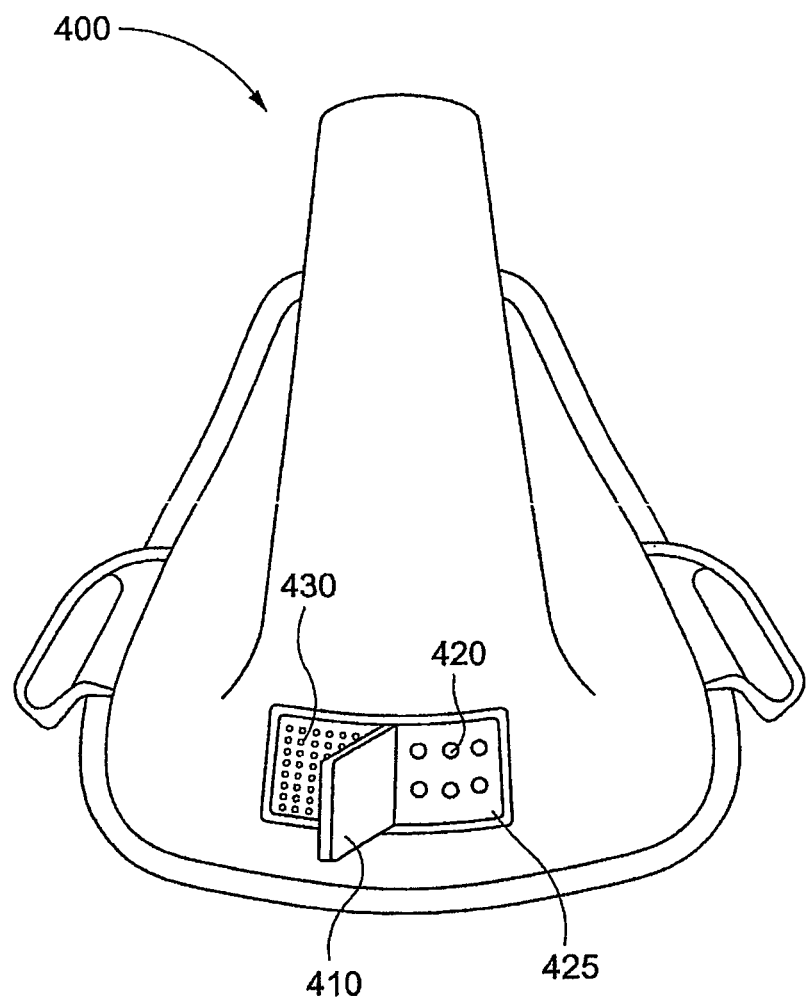
FIG. 24 shows an embodiment of the invention with a hinged vent cover.

FIG. 24 shows an alternative form of the invention in a nasal mask 400. This form of the invention includes a hinged vent cover 410. In the form shown in FIG. 24, the vent cover is generally rectangular and one side is hinged. Similarly to the vent assembly shown in FIGS. 22 and 23, the holes of FIG. 24 may be moulded into a removably insertable grommet 425. The vent cover 410 can alternatively block the set of small vent holes 430 and the set of large vent holes 420.

Figure 25A:
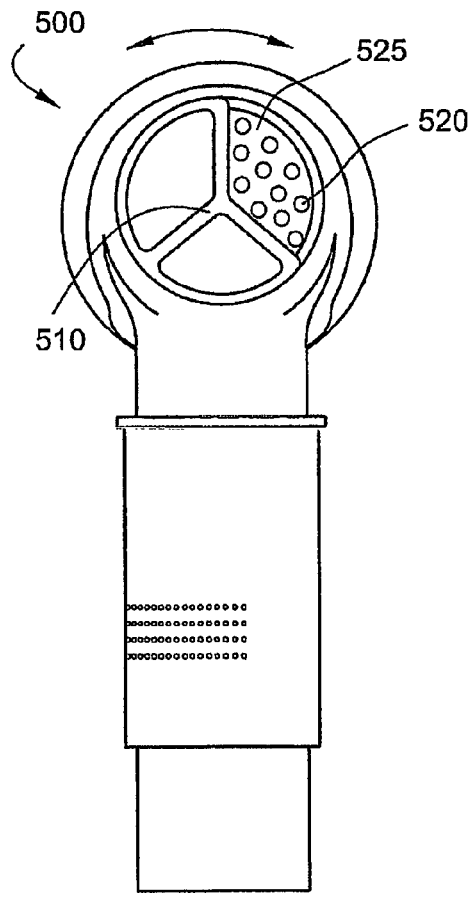
FIGS. 25a and 25b show an alternative embodiment of the invention incorporating a rotating vent cover.
Figure 25B:
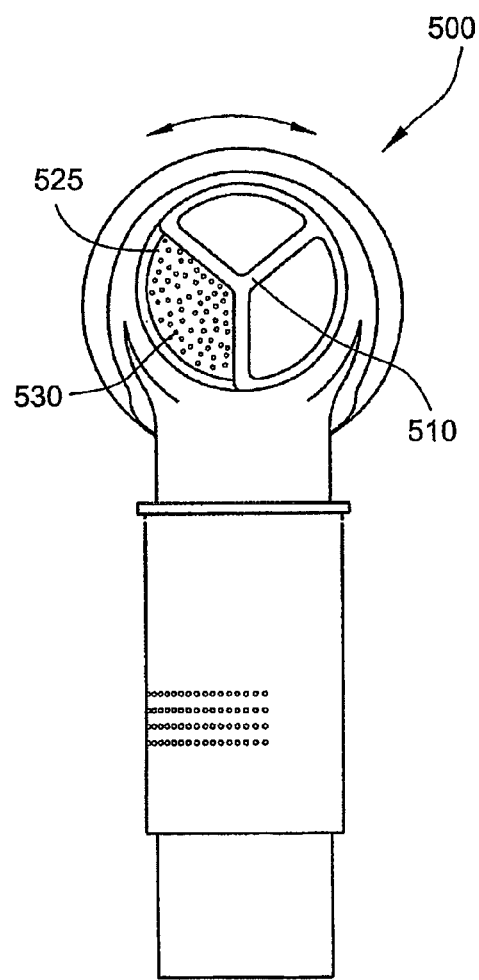

FIGS. 25a and 25b show an embodiment of the invention 500 incorporating a rotating vent cover 510 in a first and second position respectively on a vent elbow. The vent cover 510 is generally disc shaped having a window 525 therethrough. By rotating the vent cover 510 through, for example 120° different sets of holes are exposed. In the view shown in FIG. 25a, a set of large holes 520 are exposed. In the view shown in FIG. 25b a set of small holes 530 are exposed. Each respective set of holes 520, 530 provides a conduit communicating with an interior of the mask. In an alternative form (not shown) the rotatable vent cover includes different sets of holes and there is a fixed position window to which the vent cover is attached. Rotating the vent cover presents a different set of vent holes to the window resulting in a different vent characteristic.

Figure 25C:
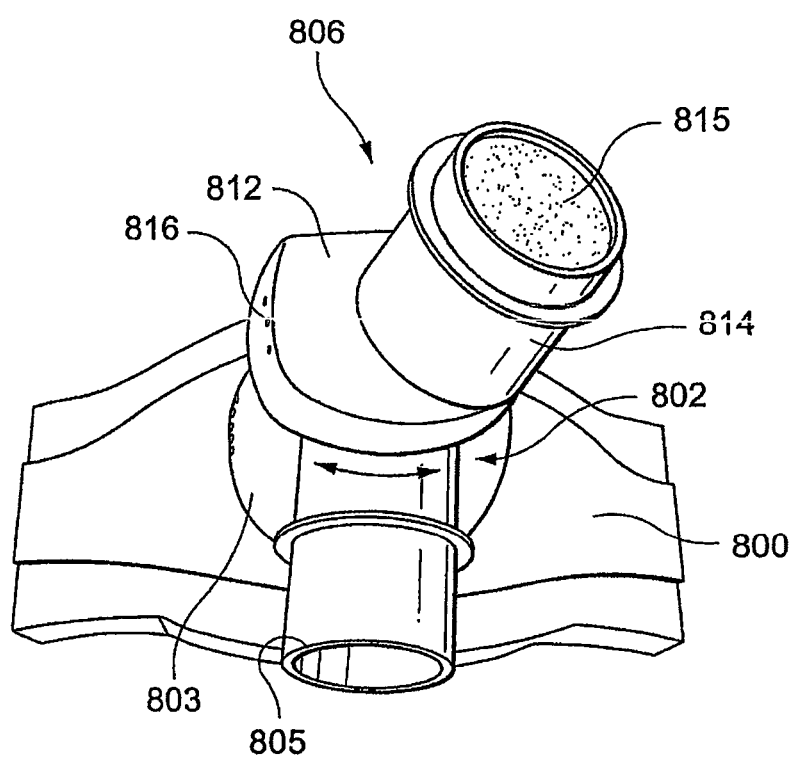
FIGS. 25c-25e illustrates another alternative embodiment of the present invention.
Figure 25D:
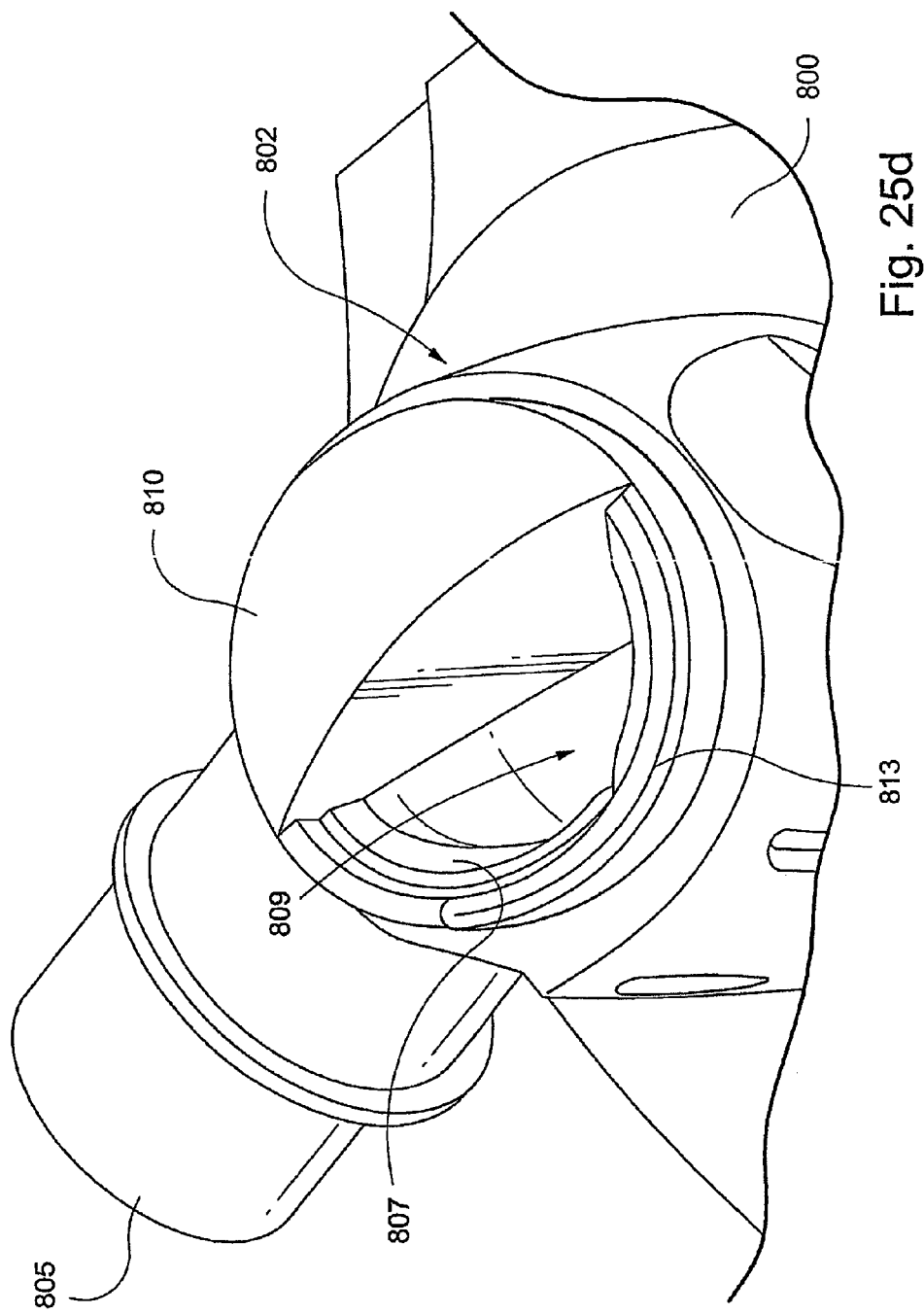
Figure 25E:
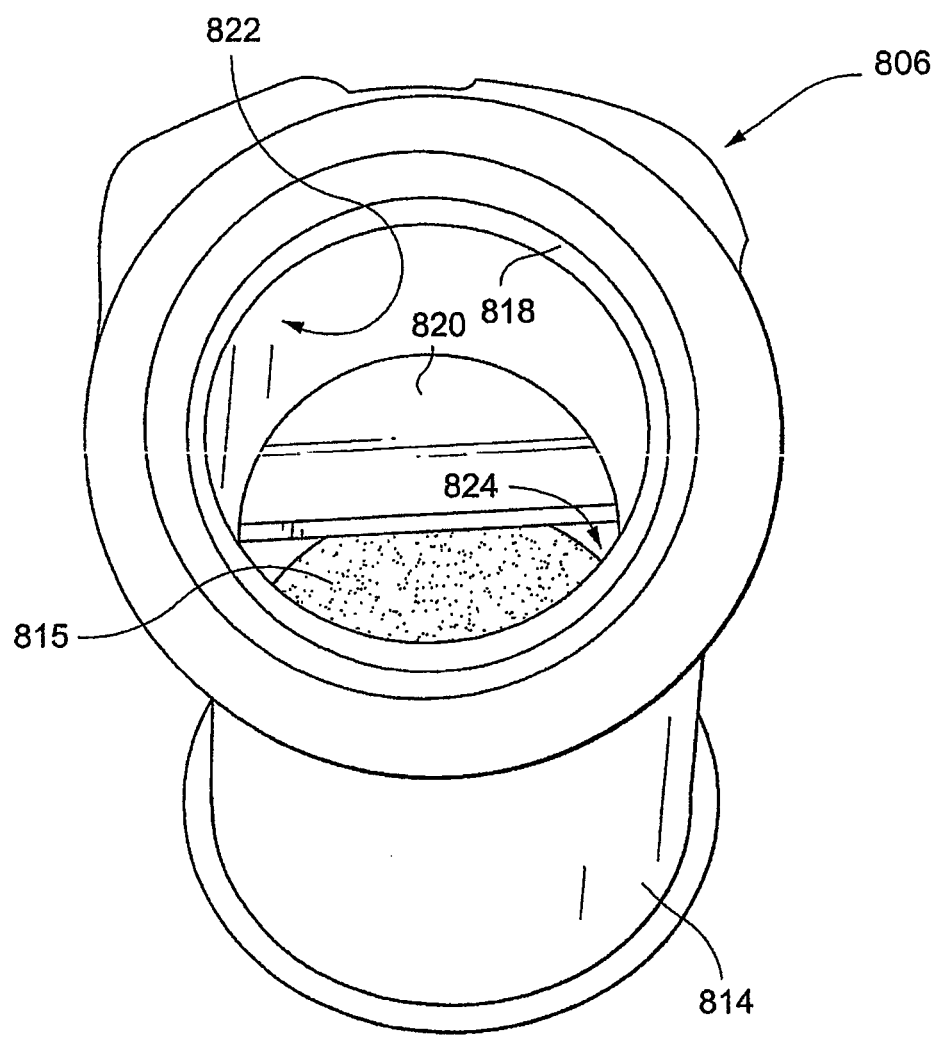

FIGS. 25c-25e illustrate yet another embodiment of the present invention. As shown in the assembled view of FIG. 25c, a frame 800 includes a swivel elbow 802 that may rotate with respect to the frame 800. A rear end 803 of the swivel elbow is connected or provided to the frame 800, while the a lower end 805 is connected to a source of pressurized air or other breathable gas. A vent assembly 806 may be provided to a front portion of the elbow 802.

Figure 7:
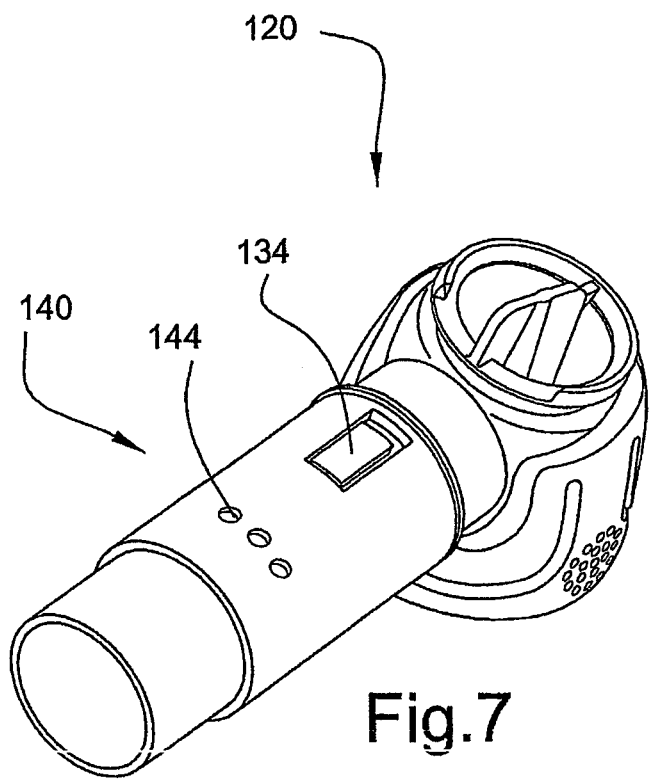
FIG. 7 shows a swivel elbow assembly in accordance with a second embodiment of the invention with the vent in a "coarse" hole position.
Figure 8:
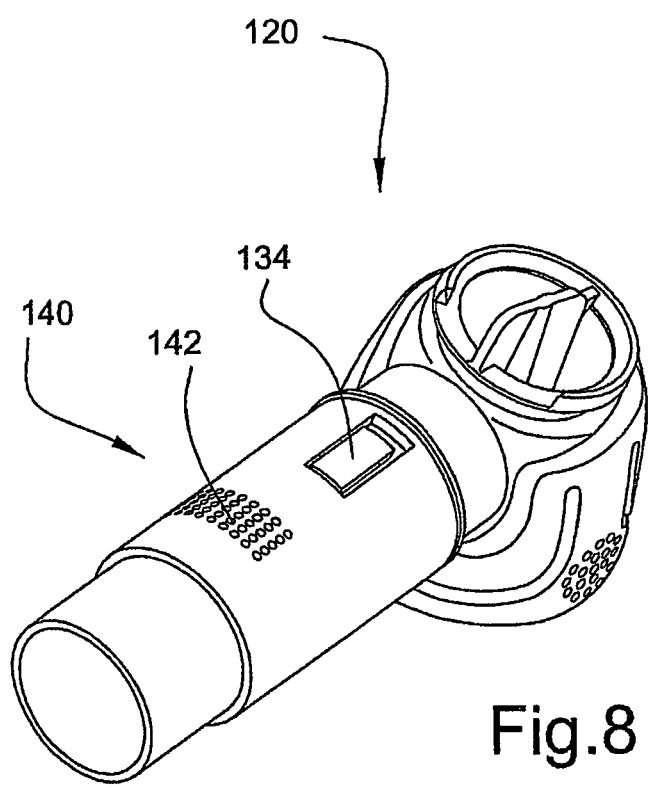
FIG. 8 shows a swivel elbow assembly in accordance with a second embodiment of the invention with the vent in a "fine" hole position.
Figure 9:
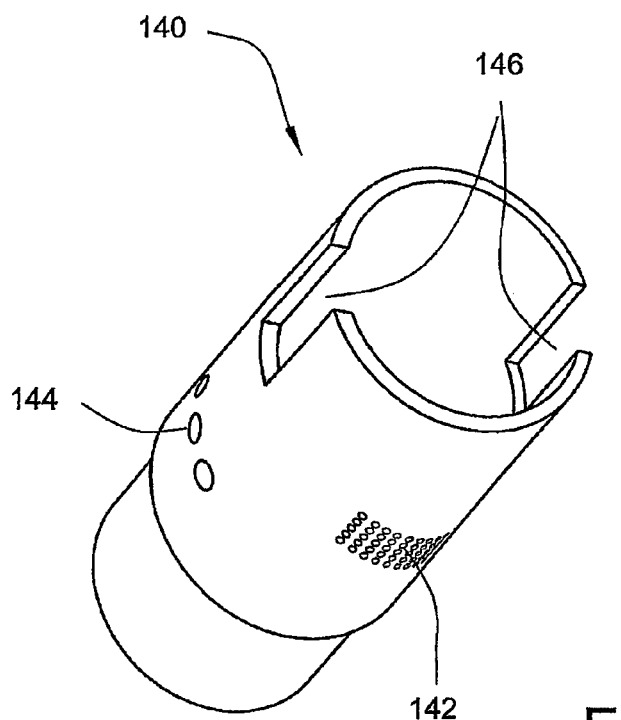
FIG. 9 shows a swivel elbow sleeve in accordance with a second embodiment of the invention.
Figure 10:
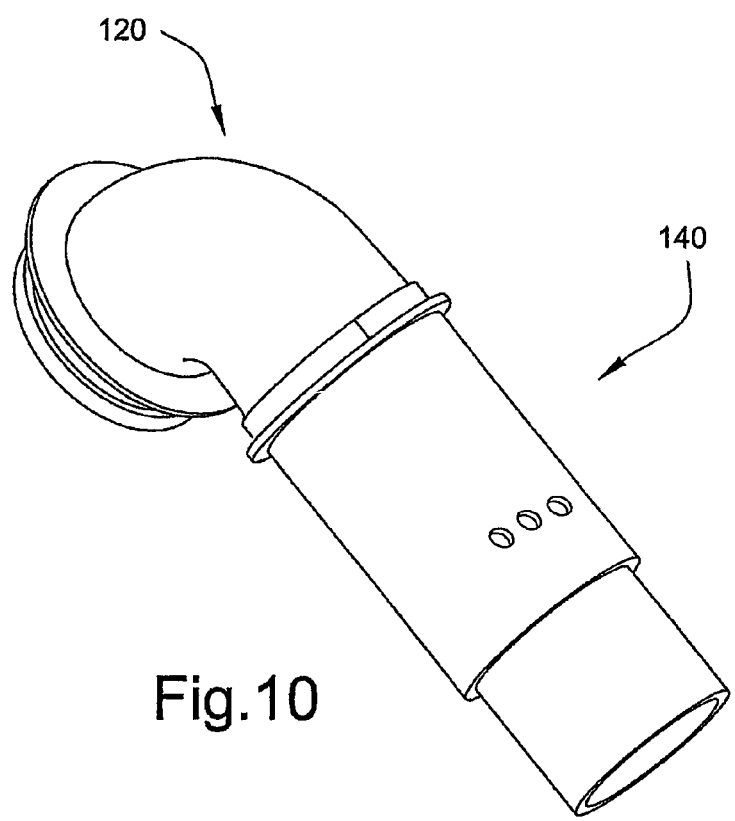
FIG. 10 shows a swivel elbow assembly in accordance with another embodiment of the invention, suitable for use with a RESMED ULTRA MIRAGE mask.

FIG. 25d shows the frame 800 and elbow 802 without the vent assembly 806. Front portion 807 of elbow 802 is similar to that shown in FIG. 7, in that it includes a vent opening 809 that continuously exhausts $CO_2$ to atmosphere. In the case of FIG. 7, exhausted air is initially directed to vent cover 70 (see FIG. 2) provided to cover the front portion of the elbow, and then the exhausted air is directed to atmosphere via one or more apertures 50.

As shown in FIG. 25d, at least a portion 810 is closed or blocked, so that air may not pass therethrough. Thus, exhausted air is directed solely through that portion of the elbow including vent opening 809. Once air is exhausted through opening 809, it is directed to vent assembly 806. In particular, the exhaust can be selectively directed to either first vent portion 812 or second vent portion 814, as shown in FIG. 25c.

First vent portion 812 may be similar to the vent cover in FIG. 2, in that it can be made of an elastomeric material that is stretched to fit over a lip 813 provided to the front portion 807 of elbow 802. The first vent portion 812 may include one or more apertures 816 to exhaust exhaled gas. The first vent portion 812, unlike the vent cover in FIG. 2, may rotate with respect to the elbow 802. Rotation allows the user or clinician to select whether exhausted gas is directed to the first or second vent portion 812, 814.

FIG. 25e shows vent assembly 806 in isolation. Vent assembly 806 an opening 818 adapted to be engaged with the rim 813 positioned on front portion of elbow 802. Vent assembly includes an interior wall member 820 which partially divides the second vent portion 814 from a chamber 822 in communication with first vent portion 812. The chamber 822 and the second vent portion 814 can be in communication with one another via interior aperture 824, depending on the relative position of the vent assembly 806 with respect to the elbow 802.

For example, if the vent assembly is rotated so that the interior wall member 820 is aligned with blocked portion 810 of elbow 802 (FIG. 25d) and the aperture 824 is aligned with aperture 809, then exhausted gas can be directed through second vent portion 814. In this position, a portion of the exhaust could also be vented through first vent portion 812. If the aperture 824 is aligned with blocked portion 810, then exhausted air would be directed solely to first vent portion 810. Preferably, the blocked portion 810 may include an elastic material that can easily form an air tight seal with respect to aperture 824.

The second vent portion 808 may be in the form of a cylinder that could be filled with foam 815, to reduce noise and/or the possibility of cross-infection. As an alternative to foam, a ceramic material or GORE-TEX™ could be used.

Figure 25F:
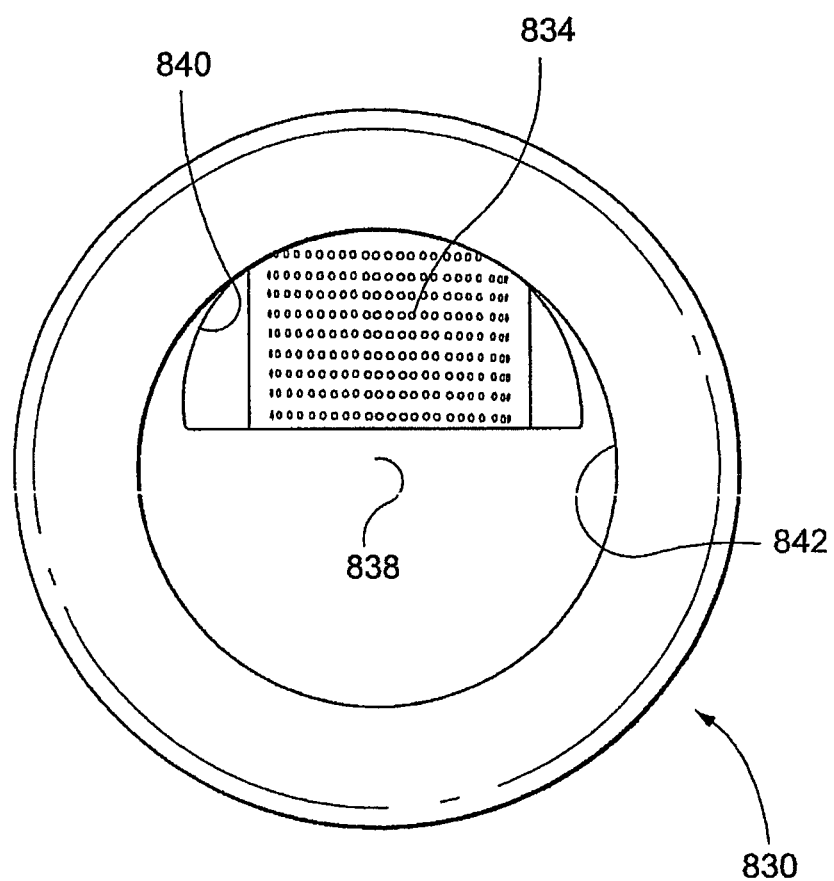
FIGS. 25f-25g illustrate yet another embodiment of the present invention.
Figure 25G:
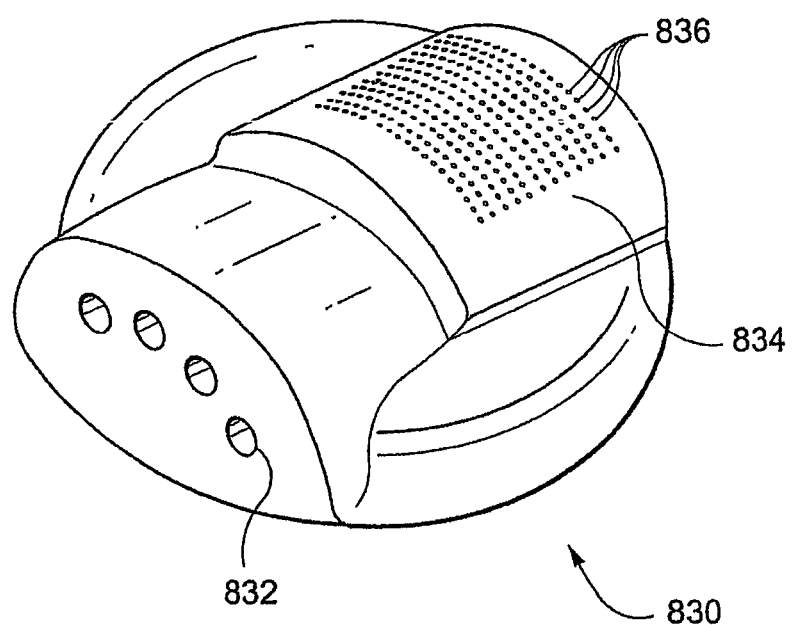

FIGS. 25f and 25g show yet another vent assembly 830, which, e.g., is adapted for use with the frame and elbow shown in FIG. 25d. Vent assembly includes a first vent portion 832 (FIG. 25g) like first vent portion shown in FIG. 25c. Vent assembly 830 includes a second vent portion 834 which includes a plurality of apertures 836. Exhausted air is selectively directed to the first or second vent portion, depending on the member 838 being selectively aligned with either the aperture 809 or the blocked portion 810 of elbow 802 (FIG. 25d). In FIG. 25f, the second vent portion 834 can be seen through aperture 840. FIG. 25f also shows opening 842 adapted to be engaged with rim 813 (FIG. 25d). The vent assembly 830 is more compact than the vent assembly shown in FIG. 25e.

Figure 26:
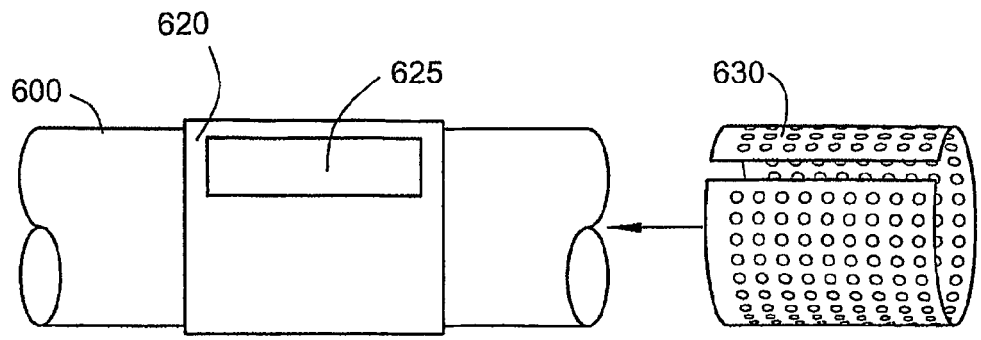
FIG. 26 shows a cartridge-style embodiment of the invention in exploded view.
Figure 27A:
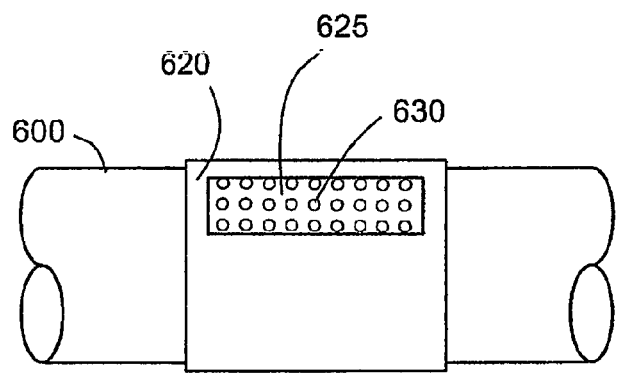
FIGS. 27a and 27b show the cartridge-style embodiment of the invention in two different positions.
Figure 27B:
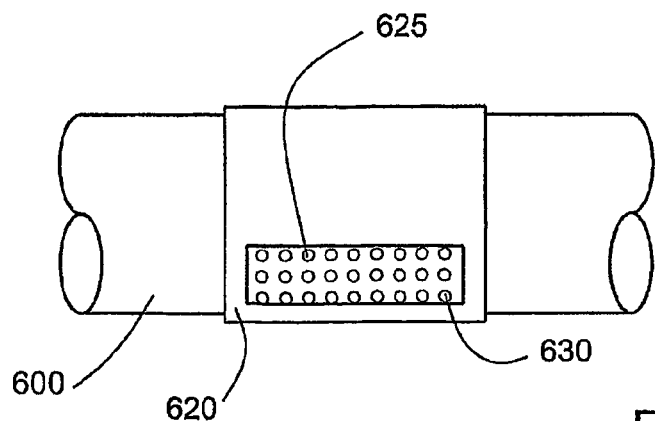

FIGS. 26, 27a and 27b show an alternative form of the invention including a replaceable vent cartridge. In this form of the invention the vent assembly comprises a shaft 600, a rotatable sleeve 620 including a window 625 and a replaceable cartridge 630 with holes therethrough. The vent assembly is shown in exploded view in FIG. 26. When assembled, the cartridge 630 is slid into position over the shaft 600 and under the sleeve 620. In the form shown in FIG. 27a-27b, in use the cartridge 630 is designed to be not rotatable about a longitudinal axis of the shaft 600. In contrast, the sleeve 620 is designed to be so rotatable exposing a different set of holes in the cartridge 630 as shown in FIGS. 27a and 27b. In use the holes of the cartridge 630 provide for fluid communication from the interior of the shaft 600 to atmosphere. Because small vent holes can become clogged with use, the sleeve 620 can be rotated after a suitable period (e.g. overnight). One cartridge might thus provide each night a clean set of vent holes for a week without requiring cleaning. At the end of the week, the cartridge may be disposed of a replaced with a clean one.

Advantages of the invention include:

When in the quiet position (fine holes) the mask will be extremely quiet, and with no discernable air jets. This makes the mask far less disturbing to both the wearer and any bed partner.

When in the normal (large holes) position, the mask will be suitable for use with a humidifier which might clog smaller holes. When the humidifier is not needed, the vent assembly can be switched easily to the quiet, small hole vent.

The use of a moveable part means that the patient does not need to keep spare parts and is precluded from losing components or not being able to fit them.

Use of the invention enables masks to be compatible with a range of different flow generators or blowers. For example, a first flow generator or blower may be pre-programmed to operate assuming a first vent characteristic and a second blower, a second vent characteristic. Since the same mask can mimic different vent characteristics, the same mask can be used on both blowers once set to the appropriate vent.

Another advantage of the invention is to provide different vents for different pressure ranges. For example, at low pressures, it may be appropriate to have a vent with large holes in order to provide sufficient vent flow. The same vent at higher pressures would have unnecessarily high vent flow which leads to increased noise. Hence in accordance with an embodiment of the invention, when a patient is using a generally low pressure treatment, they can utilize a first vent, but when treatment pressures are higher they can use a second vent.

Another advantage of the invention is that it provides a quick and simple system of replacing disposable vents. For example, certain styles of vents may clog easily and be designed for a single night's use. In accordance with an embodiment of the invention a vent assembly can comprise a set of "single use" vents. After a first night's use, the patient can switch to the second vent. After a second night's use, the patient can switch to a third vent, and so on.

Figure 20:
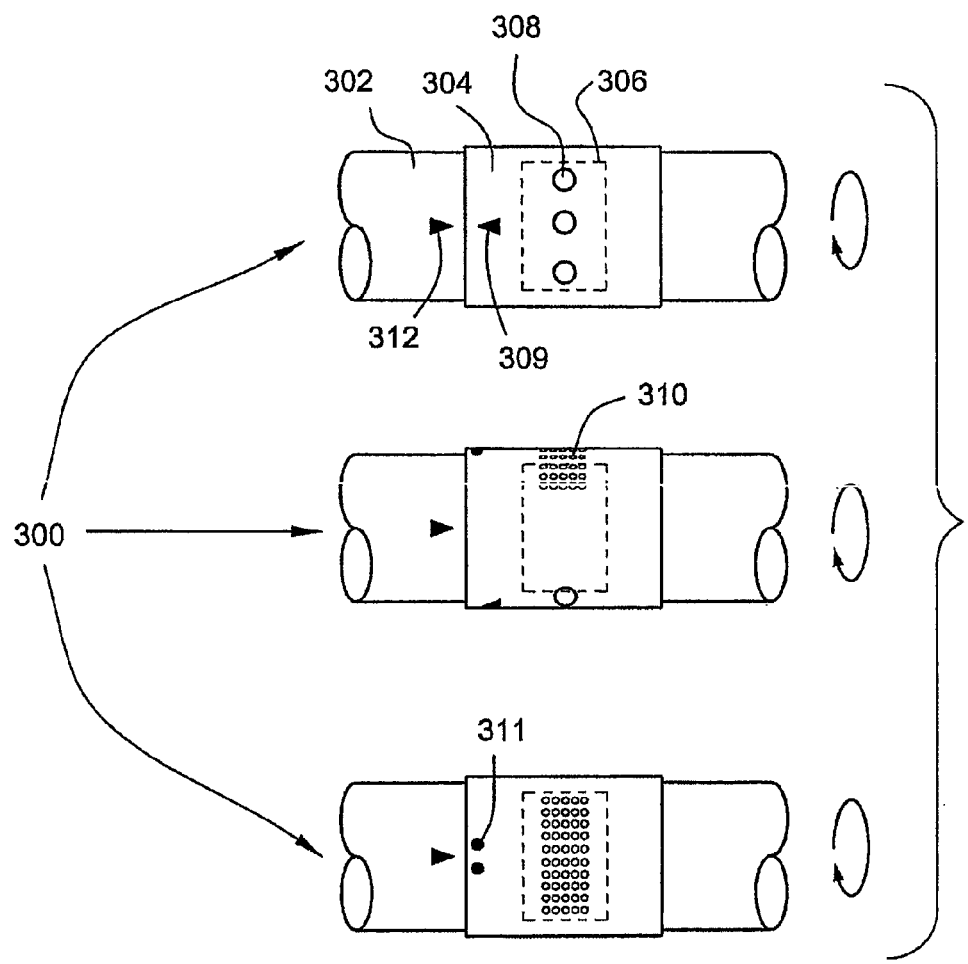
FIG. 20 shows an embodiment of the invention which incorporates visual, tactile and aural feedback of vent position.
Figure 21:
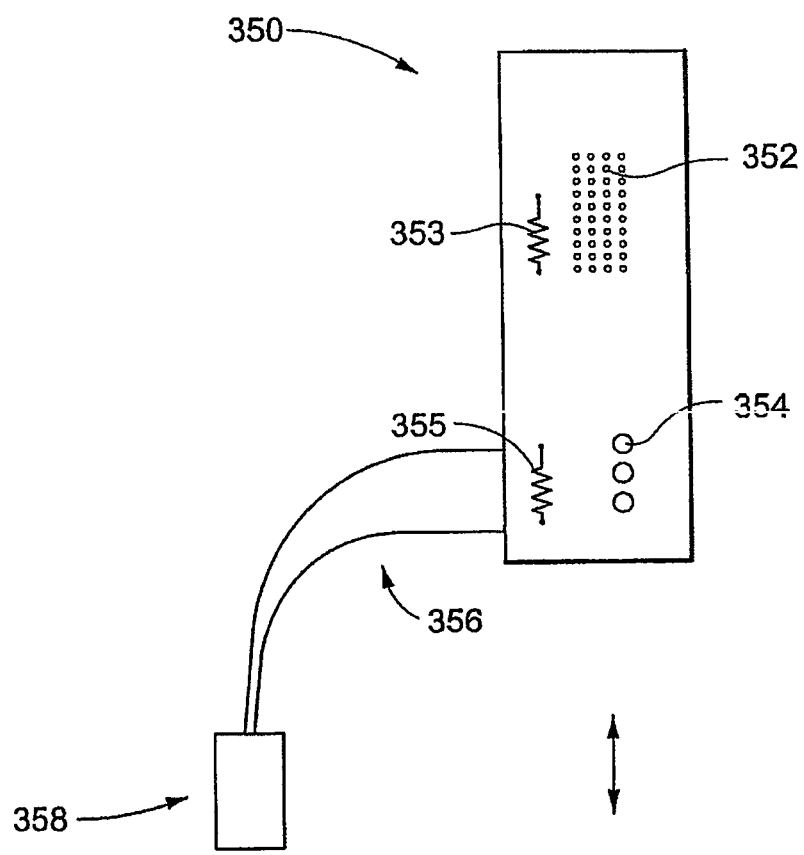
FIG. 21 shows an embodiment of the invention which incorporates an electrical resistance sensor.

In another form of the invention, sensors and/or indicators are included in the vent assembly as shown in FIGS. 20 & 21. The vent assembly 300 includes a shaft 302 and a sleeve 304. The shaft 302 includes an orifice 306 which allows air to pass through. By rotating the sleeve 304 alternative vents 308 and 310 are aligned over the orifice 306. The sensor detects which of the vents is being used and conveys the information to a flow generator controller. In one form the sensor has a different electrical resistance, depending on the vent being used, as shown in FIG. 21 and discussed further below. Sensor information may be conducted to the flow generator controller via wires along the air delivery conduit, or wirelessly, for example via a BLUETOOTH™ compatible system. The flow generator controller receives the sensor information and adjusts the parameters for the algorithms controlling therapy. Alternatively or additionally the vent assembly includes an indicator of vent position which may be visual, aural, tactile or some combination. As shown in FIG. 20, the vent assembly 300 includes an alignment arrow 312 moulded on the shaft 302. Each vent 308, 310 has an adjacent indicator (e.g. an arrow, dot or some other shape) 309, 311 molded onto the sleeve 304. The indicators may present a characteristic feel depending on the vent position so that they can be recognized in the dark. Additionally or alternatively, the vent assembly may exhibit a characteristic "click" as its vent is changed as shown in FIG. 20. The vent assembly may display a tag of different color depending on the vent position.

FIG. 21 shows schematic of a slidable cover 350 forming part of the vent assembly similar to FIG. 11-14. When the appropriate vent 352 or 354 is aligned over an orifice (not shown), a corresponding resistor 353 or 355 electrically connects to a connector 356 which is in electrical communication with a flow generator controller 358. Thus the flow generator controller 358 can detect which vent is being used and adjust pressure, flow or some other parameter of the blower as necessary.

This ability to communicate the selected vent to the flow generator allows for the flow generator to provide an appropriate response. A response may be to make an adjustment to its control algorithm taking into account the characteristic of the recognized selected vent. In addition or alternatively the flow generator may not operate in treatment mode or only operate within a predetermined pressure range when the user attempts to commence treatment having selected the less than optimum vent or the characteristics of the selected vent is not recognized by the flow generator.

In addition or alternatively the flow generator may prompt the selection of the optimum vent for a given control algorithm or air circuit configuration. Having detected the selection of a vent the flow generator may present a messages to the user. The message may be by way of an auditory or visual alarm. Through use of the flow generator status display (typically an alpha-numeric LCD panel) the flow generator may present a statement as to the detected vent condition and either confirm its appropriateness or suggest corrective action.

As the invention allows for a selection to be made between vents the flow generator may communicate to the user that a selected vent is satisfactory or unsatisfactory depending on the treatment pressure range it is set to deliver. For a higher pressure range the flow generator may prompt the use of a small hole vent while suggesting a larger hole vent where it is to operate in the lower pressure range.

If the flow generator can detect a deterioration of vent performance over time (for example due to the vent becoming blocked during one treatment session or over a number of sessions) then a prompt may be given for the selection of an alternative vent.

Such a system is of use where available air circuit configurations may include a humidifier. If the flow generator detects that a small hole (e.g. mesh vent) is selected while the air circuit is set up to operate with a humidifier the flow generator may send a message to the user in order to prompt the selection of a more suitable vent.

Flow and noise levels may thus be adjusted in accordance with the above embodiments. For example, by switching from a vent with large holes to a vent with small holes and/or foam, the flow and/or noise level can be reduced about 5-50%, preferably about 15-35%, and most preferably about 20-30%. In the embodiment of FIGS. 11a-14, the flow for large holes may be in the range of about 45-55 l/min, while the flow for the small holes may be about 55-65 l/min. In other embodiments, the difference of flow between the smaller and larger holes may be more or less pronounced, depending on patient requirements and mask configuration.

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

Figure 28A:
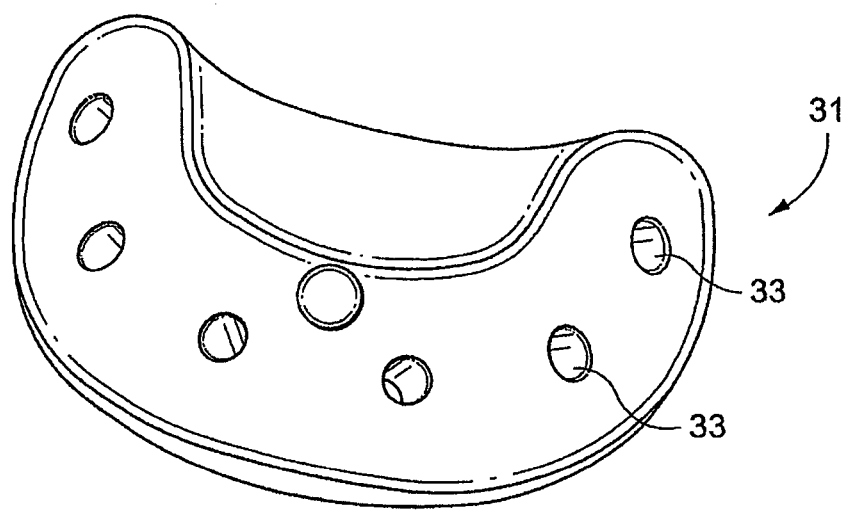
FIGS. 28a and 28b illustrate yet another embodiment of the present invention.
Figure 28B:
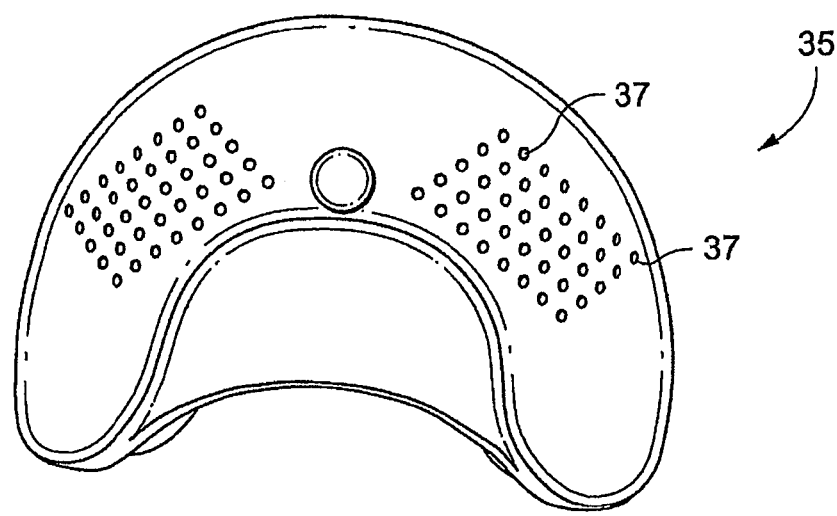

For example, in the embodiment shown in FIGS. 28a and 28b, the mask, e.g., mask 30 in FIG. 1, may be provided with two or more elastic vent inserts each having different flow characteristics. In FIG. 28a, the vent 31 has a plurality of relatively larger holes 33, while the vent 35 in FIG. 28b may have a larger number of relatively smaller holes 37. The clinician/patient may change the vent to best suit the desired noise and/or flow characteristics.

What is claimed is:
1. A mask assembly for a patient comprising:
   a frame;
   a cushion provided to the frame; and
   a vent assembly including a first vent having a plurality of first vent holes with a first venting characteristic, a second vent having a plurality of second vent holes with a second venting characteristic different from the first venting characteristic, and a selector to switch a flow of exhaled gas from the patient to the first vent holes or the second vent holes.
2. The mask assembly of claim 1, wherein the first and second venting characteristics relate to noise and/or flow which are different from one another.
3. The mask assembly according to claim 1, wherein the frame comprises a shell and the vent assembly is provided on the shell.
4. The mask assembly according to claim 1, wherein the cushion includes nozzle elements and the selector includes a clip that is slidable with respect to the frame to select between the first and second vents.
5. The mask assembly according to claim 1, wherein the selector is rotatable.
6. The mask assembly according to claim 1, wherein the selector is pivotable.
7. The mask assembly according to claim 1, wherein the selector is slidable.

8. The mask assembly according to claim 1, wherein the frame includes an elbow and the selector is provided on the elbow.

9. The mask assembly of claim 8, wherein the selector is provided on a depending arm of the elbow.

10. The mask assembly according to claim 1, wherein one of the first and second vents is provided with a material configured to reduce at least one of noise level and risk of cross-infection.

11. The mask assembly of claim 10, wherein the material is selected from the group consisting of foam, porous polytetrafluoroethylene (PTFE) and ceramic.

12. The mask assembly according to claim 1, wherein the selector is adjustable between first and second positions corresponding to the first and second vents, respectively, and the selector includes positioning structure to define the first and second positions.

13. The mask assembly of claim 12, wherein the positioning structure comprises detents.

14. The mask assembly according to claim 12, wherein the vent assembly is configured to vent exhaled gas even if the vent assembly is not in the first or second positions.

15. The mask assembly according to claim 12, wherein an alarm is sounded if the vent assembly is not in the first or second positions.

16. The mask assembly of claim 15, wherein the alarm is defined by a higher noise level produced by the vent assembly.

17. The vent assembly according to claim 1, wherein the selector is rotatable, pivotable, or slidable.

18. The mask assembly according to claim 1, wherein the first and second vents extend from an inner surface of the frame to an outer surface of the frame.

19. The mask assembly according to claim 1, wherein the plurality of first vent holes have a first size and the plurality of second vent holes have a second size smaller than the first size.

20. The mask assembly according to claim 1, wherein a number of the plurality of first vent holes is less than a number of the plurality of second vent holes.

21. The mask assembly according to claim 1, wherein selection of the second vent holes reduces flow and/or noise level by about 5-50% as compared to selection of the first vent holes.

22. The mask assembly according to claim 1, wherein selection of the first vent holes results in a flow through the first vent of about 45-55 l/min, and selection of the second vent holes results in a flow through the second vent of about 55-65 l/min.

23. The mask assembly according to claim 1, wherein the vent assembly includes a cylindrical portion having an orifice, and a sleeve portion fitting over the cylindrical portion, the sleeve portion including the first vent holes and the second vent holes, the sleeve portion being rotatable with respect to the cylindrical portion to selectively engage either the first vent holes or the second vent holes with the orifice.

24. The mask assembly according to claim 1, further comprising a swivel elbow connected to the frame, the swivel elbow including a shaft having an orifice formed therein, wherein the vent assembly is provided on a sleeve fitting over the shaft, and the sleeve is rotatable with respect to the shaft to selectively engage either the first vent or the second vent with the orifice.

25. A vent assembly including a first vent having a plurality of first vent holes with a first venting characteristic, a second vent having a plurality of second vent holes with a second venting characteristic different from the first venting characteristic, and a selector to switch a flow of exhaled gas from a patient to the first vent holes or the second vent holes.

26. The vent assembly of claim 25, wherein the first and second venting characteristics relate to noise and/or flow which are different from one another.

27. The vent assembly according to claim 25, wherein one of the first and second vents is provided with a material configured to reduce at least one of noise level and risk of cross-infection.

28. The vent assembly of claim 27, wherein the material is selected from the group consisting of foam, porous polytetrafluoroethylene (PTFE) and ceramic.

29. The vent assembly according to claim 25, wherein the selector is adjustable between first and second positions corresponding to the first and second vents, respectively, and the selector includes positioning structure to define the first and second positions.

30. The vent assembly of claim 29, wherein the positioning structure comprises detents.

31. The vent assembly according to claim 29, wherein the vent assembly is configured to vent exhaled gas even if the vent assembly is not in the first or second positions.

32. The vent assembly according to claim 29, wherein an alarm is sounded if the vent assembly is not in the first or second positions.

33. The mask assembly of claim 32, wherein the alarm is defined by a higher noise level produced by the vent assembly.

34. The vent assembly according to claim 25, wherein the plurality of first vent holes have a first size and the plurality of second vent holes have a second size smaller than the first size.

35. The vent assembly according to claim 25, wherein a number of the plurality of first vent holes is less than a number of the plurality of second vent holes.

36. The vent assembly according to claim 25, wherein selection of the second vent holes reduces flow and/or noise level by about 5-50% as compared to selection of the first vent holes.

37. The vent assembly according to claim 25, wherein selection of the first vent holes results in a flow through the first vent of about 45-55 l/min, and selection of the second vent holes results in a flow through the second vent of about 55-65 l/min.

38. The vent assembly according to claim 25, further comprising a cylindrical portion having an orifice, and a sleeve portion fitting over the cylindrical portion, the sleeve portion including the first vent and the second vent, the sleeve portion being rotatable with respect to the cylindrical portion to selectively engage either the first vent or the second vent with the orifice.

39. A mask assembly for a patient comprising:
a frame;
a cushion provided to the frame;
a vent assembly provided to the frame having a first vent portion having a plurality of first vent holes with a first flow capacity and a second vent portion having a plurality of second vent holes with a second flow capacity different from the first flow capacity, and
a slidable selector to switch a flow of exhaled gas from the patient to the first vent holes or the second vent holes.

40. The mask assembly according to claim 39, wherein the plurality of first vent holes have a first size and the plurality of second vent holes have a second size smaller than the first size.

41. The mask assembly according to claim 39, wherein a number of the plurality of first vent holes is less than a number of the plurality of second vent holes.

42. The mask assembly according to claim 39, wherein selection of the second vent holes reduces flow and/or noise level by about 5-50% as compared to selection of the first vent holes.

43. The mask assembly according to claim 39, wherein selection of the first vent holes results in a flow through the first vent holes of about 45-55 l/min, and selection of the second vent holes results in a flow through the second vent holes of about 55-65 l/min.

44. The mask assembly according to claim 39, wherein the vent assembly includes a cylindrical portion having an orifice, and a sleeve portion fitting over the cylindrical portion, the sleeve portion including the first vent portion and the second vent portion, the sleeve portion being slidable as the slidable selector with respect to the cylindrical portion to selectively engage either the first vent portion or the second vent portion with the orifice.

45. The mask assembly according to claim 39, further comprising a swivel elbow connected to the frame, the swivel elbow including a shaft having an orifice formed therein, wherein the vent assembly is provided on a sleeve fitting over the shaft, the sleeve is slidable as the slidable selector with respect to the shaft to selectively engage either the first vent portion or the second vent portion with the orifice.

* * * * *

UNITED STATES PATENT AND TRADEMARK OFFICE
CERTIFICATE OF CORRECTION

PATENT NO.        : 8,678,003 B2                                        Page 1 of 1
APPLICATION NO.   : 10/579221
DATED             : March 25, 2014
INVENTOR(S)       : Darkin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1486 days.

Signed and Sealed this

Twenty-ninth Day of September, 2015

Michelle K. Lee
*Director of the United States Patent and Trademark Office*